(12) United States Patent
Xiao

(10) Patent No.: US 11,793,674 B2
(45) Date of Patent: Oct. 24, 2023

(54) CONTACT LENSES WITH BIFOCAL CHARACTERISTICS

(71) Applicant: LUTRONIC VISION INC., Burlington, MA (US)

(72) Inventor: Zhen Xiao, Beijing (CN)

(73) Assignee: LUTRONIC VISION INC.

( * ) Notice: Subject to any disclaimer, the term of this patent is extended or adjusted under 35 U.S.C. 154(b) by 920 days.

(21) Appl. No.: 16/639,825

(22) PCT Filed: Aug. 17, 2017

(86) PCT No.: PCT/CN2017/097827
§ 371 (c)(1),
(2) Date: Feb. 18, 2020

(87) PCT Pub. No.: WO2019/033334
PCT Pub. Date: Feb. 21, 2019

(65) Prior Publication Data
US 2020/0246181 A1 Aug. 6, 2020

(51) Int. Cl.
*A61F 9/008* (2006.01)
*A61B 3/125* (2006.01)
*G02C 7/04* (2006.01)

(52) U.S. Cl.
CPC .............. *A61F 9/008* (2013.01); *A61B 3/125* (2013.01); *G02C 7/041* (2013.01)

(58) Field of Classification Search
CPC A61F 9/008; A61B 3/125; A61B 3/13; G02C 7/041; G02C 7/04
See application file for complete search history.

(56) References Cited

U.S. PATENT DOCUMENTS 5,046,836 A * 9/1991 Volk .................. A61B 3/125
351/219
6,164,779 A 12/2000 Volk
(Continued)

FOREIGN PATENT DOCUMENTS

CN 102657516 A 9/2012
CN 104398236 A 3/2015
(Continued)

OTHER PUBLICATIONS

International Search Report and Written Opinion for International Application No. PCT/CN2017/097827 dated May 22, 2018, pp. 09.
(Continued)

*Primary Examiner* — Gary Jackson
*Assistant Examiner* — Sebastian X Lukjan

(57) ABSTRACT

A contact lens (318,400,500,600) may include a contact lens body (402), an exterior contact surface (322,404), and an annular bifocal surface (326,408). The contact lens (318, 400,500,600) may be configured for use in a contact lens assembly (300) for laser-based ophthalmological surgical treatments. The exterior contact surface (322,404) may be on a first end of the contact lens body (402). The exterior contact surface (322,404) may be configured for direct physical contact with a cornea (102) of an eye (100) of a patient. The annular bifocal surface (326,408) may be on a second end of the contact lens body (402). The second end may be opposite the exterior contact surface (322,404). The annular bifocal surface (326,408) may include a central portion (347,412,502,602). The central portion (347,412, 502,602) may include a first focal distance. The annular bifocal surface (326,408) may include an outer portion (349,414,504,604) that surrounds at least a portion of the central portion (347,412,502,602). The annular bifocal surface (326,408) may include a second focal distance.

17 Claims, 14 Drawing Sheets

(56) References Cited

U.S. PATENT DOCUMENTS

| | | |
|---|---|---|
| 6,698,886 B2 | 3/2004 | Pollack et al. |
| 7,115,120 B2 | 10/2006 | Lin |
| 7,836,894 B2 | 11/2010 | Brinkmann et al. |
| 9,016,860 B2 | 4/2015 | Peyman |
| 9,301,681 B2 | 4/2016 | Ha et al. |
| 2013/0315374 A1* | 11/2013 | Gertner .................. A61F 9/008 378/65 |
| 2015/0164686 A1 | 6/2015 | Ha et al. |
| 2015/0202083 A1* | 7/2015 | Takeda .................. A61B 18/20 606/4 |
| 2015/0342459 A1 | 12/2015 | Robert et al. |

FOREIGN PATENT DOCUMENTS

| | | | |
|---|---|---|---|
| WO | 2014/106330 A1 | 7/2014 | |
| WO | WO-2016196200 A1 * | 12/2016 | ............... A61F 9/00 |

OTHER PUBLICATIONS

Kim, H.D., et al., "Retinal Pigment Epithelium Responses to Selective Retina Therapy in Mouse Eyes," Investigative Ophthalmology & Visual Science, vol. 57, No. 7, pp. 3486-3495 (Jun. 1, 2016).

* cited by examiner

CONTACT LENSES WITH BIFOCAL CHARACTERISTICS

CROSS-REFERENCE

This patent application is a section 371 nationalization of PCT Application No. PCT/CN2017/097827 filed Aug. 17, 2017, which PCT application is incorporated herein by specific reference in its entirety.

BACKGROUND

Unless otherwise indicated herein, the materials described herein are not prior art to the claims in the present application and are not admitted to be prior art by inclusion in this section.

Macula disease may result in loss of vision or reduction in quality of vision of a patient. Diabetic macular edema (DME), age-related macular degeneration (AMD), and central serous chorioretinopathy (CSC) are examples of macula disease. In some circumstances, therapeutic radiation may be administered to an eye of a patient to treat the macula disease. Prior to administration of the therapeutic radiation, a fundus image may be acquired. Diagnosis of the macula disease may be based on the fundus image. Following diagnosis, a laser-based ophthalmological treatment system (hereinafter, "treatment system") may be used in combination with a contact lens assembly to administer the therapeutic radiation. In some treatment systems, there may be no effective reference found in a visual field. The lack of an effective reference may be due in part to a relatively small observing area provided by the contact lens assembly.

SUMMARY

Techniques described herein generally relate to therapeutic radiation treatment systems and methods.

In an example embodiment, a contact lens may include a contact lens body, an exterior contact surface, and an annular bifocal surface. The contact lens may be configured for use in a contact lens assembly for laser-based ophthalmological surgical treatments. The exterior contact surface may be on a first end of the contact lens body. The exterior contact surface may be configured for direct physical contact with a cornea of an eye of a patient. The annular bifocal surface may be on a second end of the contact lens body. The second end may be opposite the exterior contact surface. The annular bifocal surface may include a central portion. The central portion may include a first focal distance. The annular bifocal surface may include an outer portion that surrounds at least a portion of the central portion. The annular bifocal surface may include a second focal distance.

In another example embodiment, a contact lens assembly may include an assembly housing, an input lens, and a contact lens. The contact lens assembly may be configured for implementation in laser-based treatment. The assembly housing may define a first opening and a second opening that is opposite the first opening. The input lens may be positioned in the first opening. The contact lens may be positioned in the second opening. The contact lens may include an exterior contact surface configured for direct physical contact with a cornea of an eye of a patient. The contact lens may include an annular bifocal surface that includes a central portion having a first focal distance and an outer portion that surrounds at least a portion of the central portion having a second focal distance.

In yet another example embodiment, a laser-based ophthalmological surgical system may include a therapeutic radiation source, a contact lens assembly, a head fixation assembly, and a microscope. The contact lens assembly may be optically coupled to the therapeutic radiation source. The contact lens assembly may include a contact lens. The contact lens may include an annular bifocal surface having a central portion having a first focal distance and an outer portion that surrounds at least a portion of the central portion having a second focal distance. The head fixation assembly may be configured to position and retain a head of a patient with an eye of the patient optically aligned to the contact lens assembly to receive therethrough therapeutic radiation emitted by the therapeutic radiation source. The microscope may be optically coupled to the contact lens assembly. The microscope may be optically coupled to the contact lens assembly to allow an operator of the laser-based ophthalmological surgical system to view the eye of the patient during therapeutic treatment of the eye of the patient with the laser-based ophthalmological surgical system.

In another example embodiment, a method of image-based fundus alignment implemented during a laser-based ophthalmological treatment may include placing a contact lens assembly on an eye of a patient. The contact lens assembly may be placed in an optical path that may be optically aligned with a therapeutic radiation source and a photography device. The method may include receiving, by the photography device, light transmitted through the contact lens assembly. The received light may include a first portion reflected from a portion of a fundus of the eye and transmitted through a central portion of a contact lens. The received light may include a second portion reflected from a portion of an iris and transmitted through an outer portion of the contact lens. The method may include capturing, by the photography device, a fundus image based on the received light. The fundus image may include the portion of the fundus and the portion of the iris.

In some embodiments, a contact lens can be configured for use in a contact lens assembly for laser-based ophthalmological surgical treatments. The contact lens can include: a contact lens body; an exterior contact surface on a first end of the contact lens body, wherein the exterior contact surface is concave and configured for direct physical contact with a cornea of an eye of a patient; and an annular bifocal surface on a second end of the contact lens body that is opposite the exterior contact surface. In some aspects, the annular bifocal surface includes: a central portion that has a central convex surface that includes a first focal distance; an outer portion that surrounds at least a portion of the central portion and includes at least one outer surface that has a second focal distance; and a transition between the central convex surface and the at least one outer surface. In some aspects, the central portion is positioned on a primary optical path that is configured to be aligned with a pupil of the eye during one or both of an imaging process and a treatment process. In some aspects, the outer portion is positioned on a secondary optical path that is radially displaced relative to the primary optical path. In some aspects, the secondary optical path is configured to be optically aligned with a portion of an iris that surrounds the pupil during one or both of the imaging process and the treatment process. In some aspects, the at least one outer surface of the outer portion includes at least one concentric annular section defined in the annular bifocal surface with the central portion. In some aspects, the at least one outer surface of the outer portion includes a Fresnel lens. In some aspects, the at least one outer surface of the outer portion includes a microlens array. In some aspects, the at least one outer surface of the outer portion includes a second convex surface. In some embodiments, a laser-based ophthalmological surgical system can include: a therapeutic radiation source; a contact lens assembly optically coupled to the therapeutic radiation source; a head fixation assembly configured to position and retain a head of a patient with an eye of the patient optically aligned to the contact lens assembly to receive therethrough therapeutic radiation emitted by the therapeutic radiation source; and a microscope optically coupled to the contact lens assembly. In some aspects, the contact lens assembly comprises a contact lens that includes an annular bifocal surface. Ins some aspects, the annular bifocal surface can include: a central portion that has a central convex surface with a first focal distance; an outer portion that surrounds at least a portion of the central portion and includes at least one outer surface that has a second focal distance; and a transition between the central convex surface and the at least one outer surface.

In some embodiments, the contact lens assembly further comprises: an assembly housing; and an input lens positioned in a first opening that is defined in the assembly housing. In some aspects, the contact lens is positioned in a second opening that is defined in the assembly housing.

In some aspects, the at least one outer surface of the outer portion includes at least one of: a concentric annular section; a microlens array; a Fresnel lens; or a second convex surface.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1A:
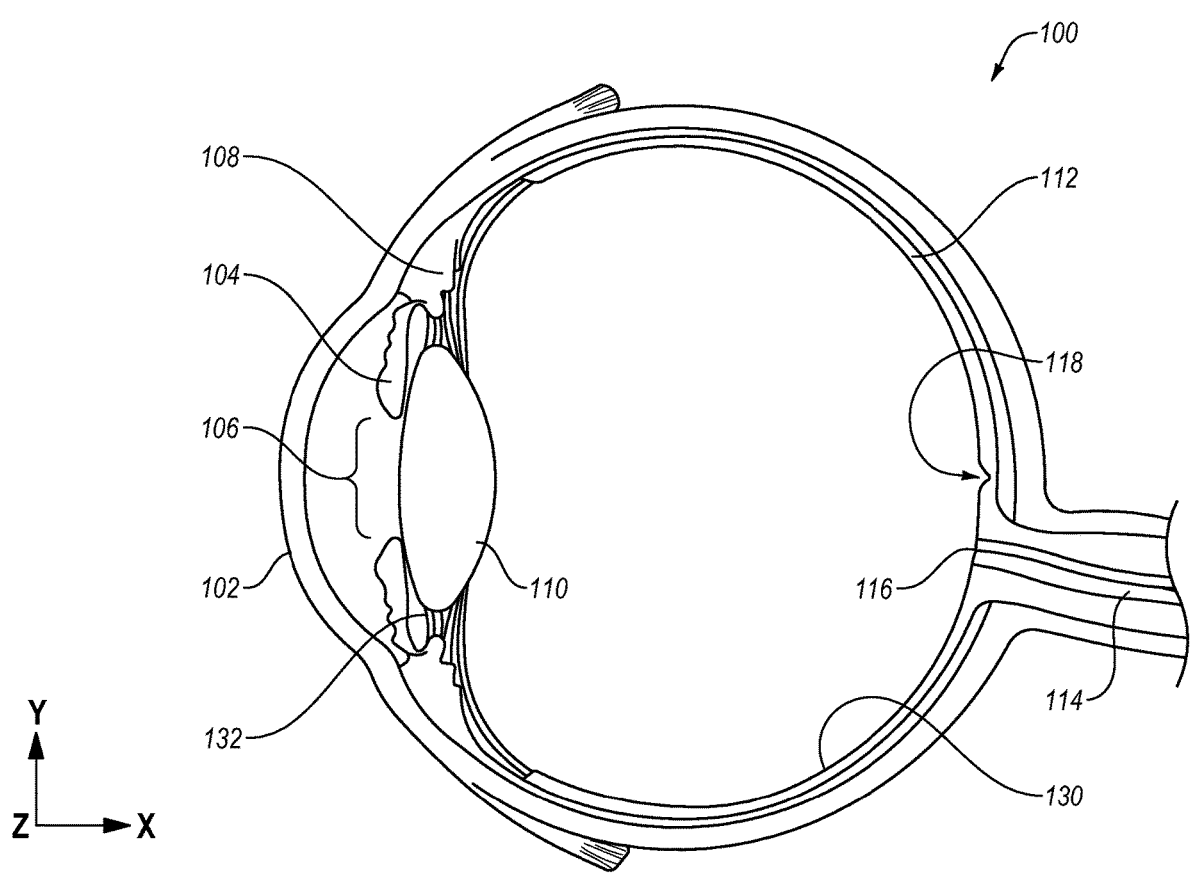
FIG. 1A is a cross-sectional view of an example human eye (hereinafter "eye")

This disclosure is generally drawn to methods, apparatus, systems, devices, and computer program products related to therapeutic radiation dosimetry.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

Macula disease such as diabetic macular edema (DME), age-related macular degeneration (AMD), and central serous chorioretinopathy (CSC) may result in vision impairment or vision loss. Diagnosis of macula disease may be performed based on images of a fundus of an eye. Some example fundus images may include a fundus fluorescein angiography (FFA), an indocyanine green chorioangiography (ICG), or another fundus image. Based on the fundus image, a healthcare provider may identify a diseased portion of the eye or an abnormality that may be indicative of macula disease. Fundus images generally include only an image of the fundus. For example, the fundus image is generated based on light that is reflected from the fundus out of the eye, through the pupil. The inclusion of only the light from the fundus is due to a narrow visual field of a contact lens assembly used to acquire the fundus image.

Accordingly, in some embodiments described herein, a system is described that may be configured to generate fundus images that may include a portion of the fundus along with a portion of the iris. For example, some embodiments may include a contact lens with bifocal characteristics. The contact lens may include a central portion that receives light reflected from the fundus of the eye. The contact lens also includes an outer portion that surrounds at least a portion of the central portion. For instance, the outer portion may be an annular structure that surrounds the central portion. The outer portion receives light reflected from a portion of the iris that surrounds a pupil. Thus, a fundus image generated using the contact lens may include a portion of the fundus along with a portion of the iris.

The portion of the iris may include features and patterns that are unique or substantially unique to a rotational position of the eye. Thus, the portion of the iris may be used as a reference. For instance, the diseased portion of the fundus or the abnormality may be located based on the portion of the iris.

Treatment of the macula disease may involve administration of a therapeutic radiation by a laser-based ophthalmological treatment system (treatment system). The therapeutic radiation may be emitted through the contact lens assembly, through a pupil of the eye, and to the diseased portion of the fundus. A surface of the contact lens of the contact lens assembly may be placed in direct physical contact with a cornea of the eye. Prior to administration of the therapeutic radiation, a radiation source may be aligned with the diseased portion or the abnormality on the fundus.

In some embodiments, alignment of the radiation source may be based on the portion of the iris that surrounds the pupil. For example, during treatment, the contact lens assembly may be placed on the cornea of the eye. The contact lens assembly may include the contact lens that has the bifocal characteristics. Accordingly, light reflected from a portion of the iris may be received. As mentioned above, during diagnosis based on the fundus image, the diseased portion or the abnormality may be located using the portion of the iris or features thereon as a reference. The treatment system may compare the light reflected from the portion of the iris with the portion of the iris included in the fundus image. Based on a comparison, the radiation source may be aligned with the abnormality using the light reflected from the portion of the iris as a reference.

FIG. 1A is a cross-sectional view of an example human eye (hereinafter "eye") 100. The eye 100 may include a cornea 102, an iris 104, a pupil 106, a ciliary body 108, a lens 110, a retina 112, a fundus 130, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

The fundus 130 of the eye 100 includes an interior surface of the eye 100 opposite the lens 110. The fundus 130 may include a portion of the retina 112. The retina 112 includes an optic disc 116, sometimes referred to as the "blind spot." The retina 112 may also include a macula 118. The macula 118 may be separated from the optic disc 116 on the retina 112.

The eye 100 may rotate in a socket to view an object. Rotation of the eye 100 may orient the pupil 106 and the retina 112 to receive light from the object. The pupil 106 allows the light to enter the eye 100. When the eye 100 moves, the pupil 106 and the retina 112 may move in the y-direction and/or the z-direction of an arbitrarily defined Cartesian coordinate system of FIG. 1A. Additionally, in response to the light, a diameter of the pupil 106 may change.

The ciliary body 108 may be attached to the lens 110 via zonula fibers 132. The ciliary body 108 may change a shape of the lens 110 as the eye 100 focuses on the object. The shape of the lens 110 may dictate how the light strikes the retina 112.

Figure 1B:
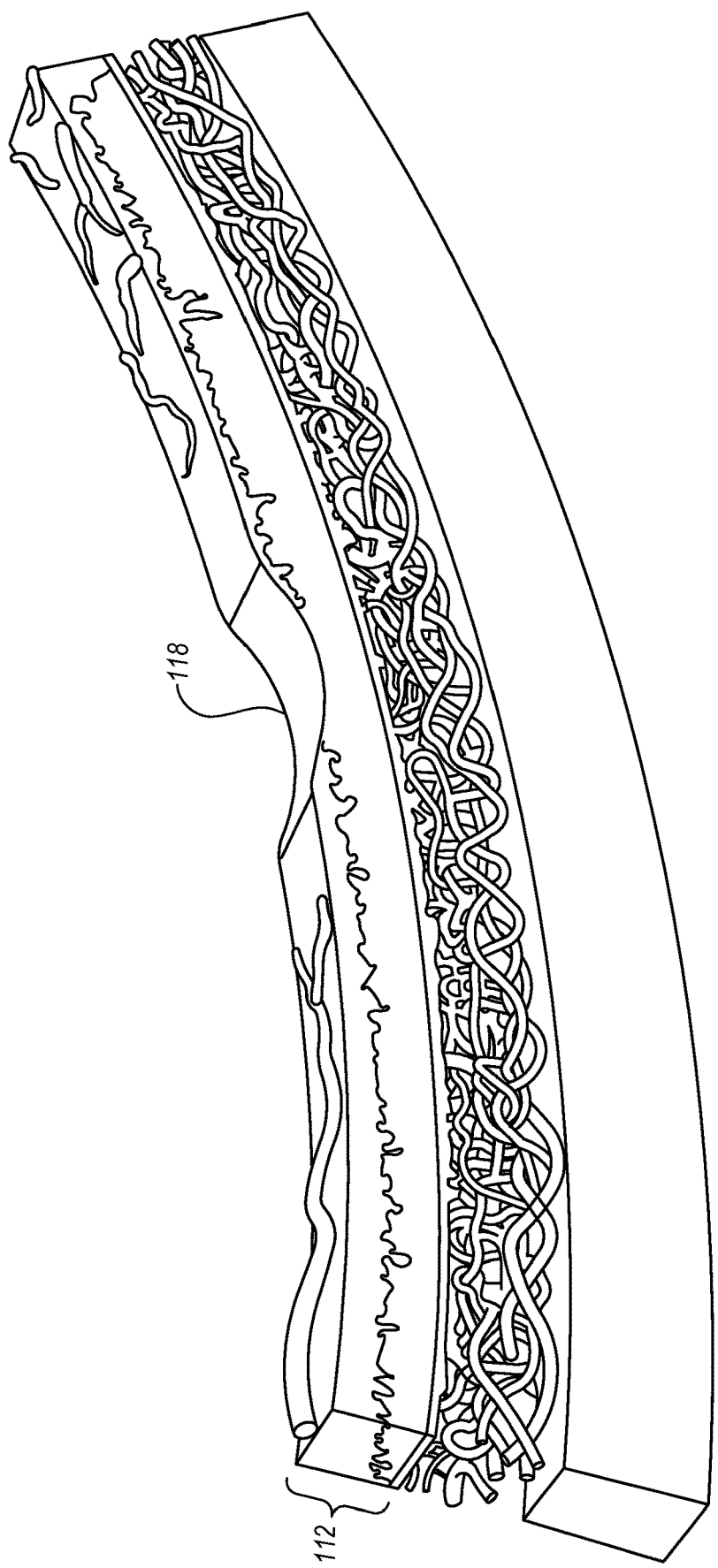
FIG. 1B is a cross-sectional perspective view of a portion of a retina and a macula of FIG. 1B.

FIG. 1B is a cross-sectional perspective view of a portion of the retina 112 and the macula 118 of FIG. 1A.

Figure 1C:
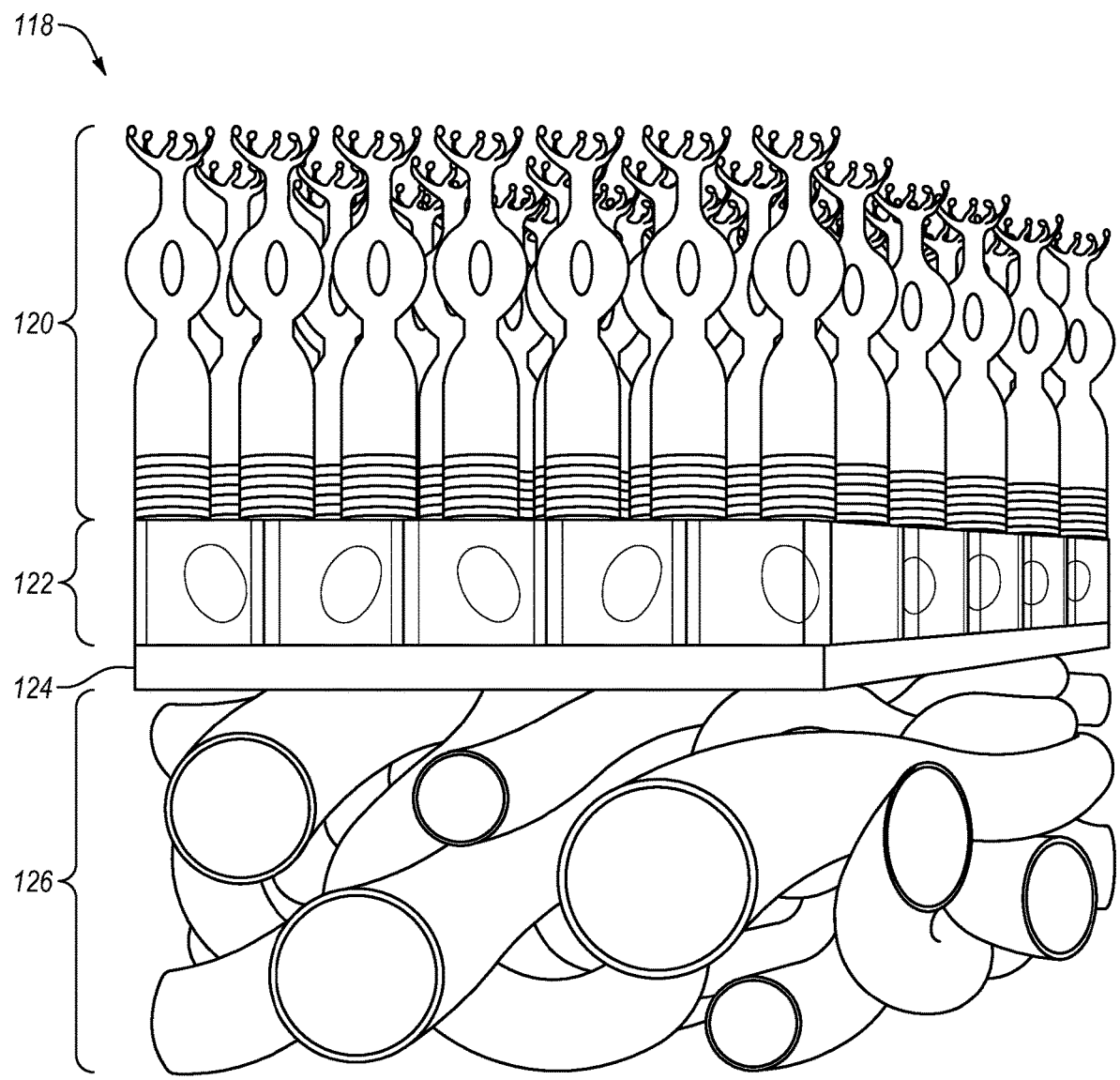
FIG. 1C is a cross-sectional perspective view of a portion of the macula of FIG. 1B.

FIG. 1C is a cross-sectional perspective view of a portion of the macula 118 of FIG. 1B. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high-resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, AMD may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be DME. In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be CSC. In CSC, leakage of fluid accumulates under the central macula 118, resulting in blurred or distorted vision, which may progressively decline with each recurrence.

Some embodiments described herein include a laser-based ophthalmological treatment system that includes a therapeutic radiation source configured to emit therapeutic radiation to treat AMD, DME, CSC, and/or other conditions of the eye 100.

Figure 2A:
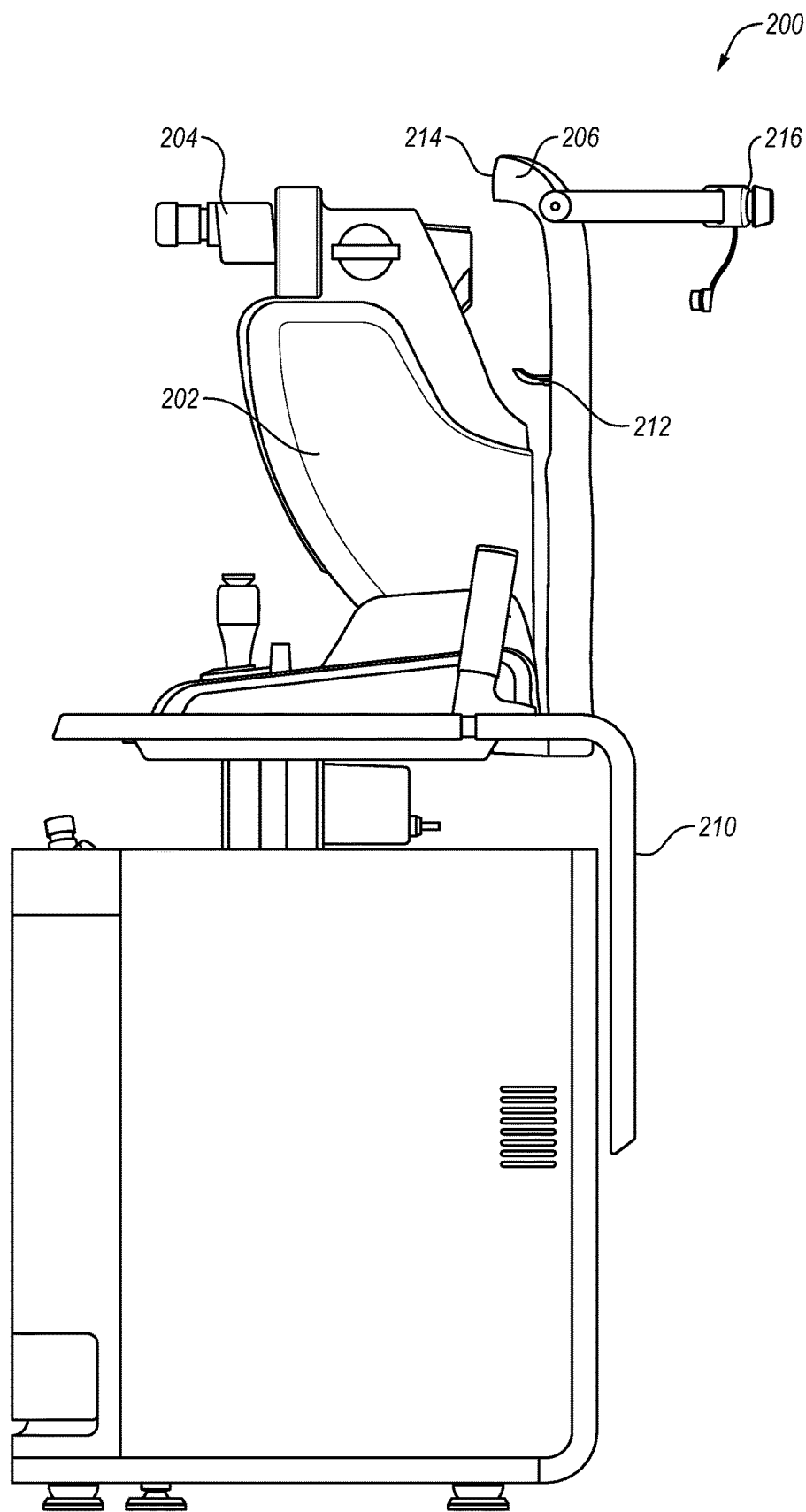
FIG. 2A illustrates an example laser-based ophthalmological surgical system (hereinafter "system")
Figure 2B:
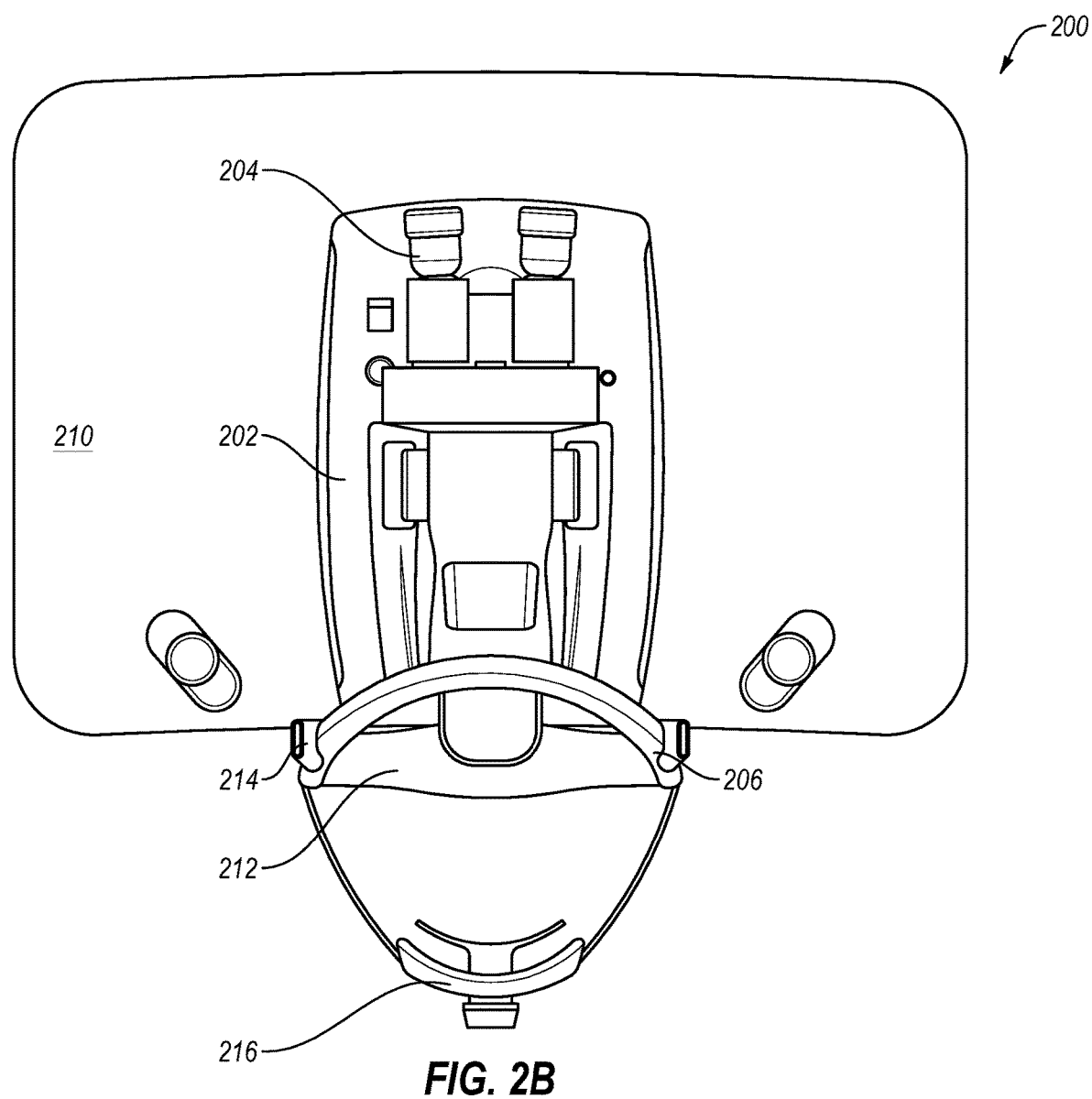
FIG. 2B illustrates another view of the system of FIG. 2A.
Figure 2C:
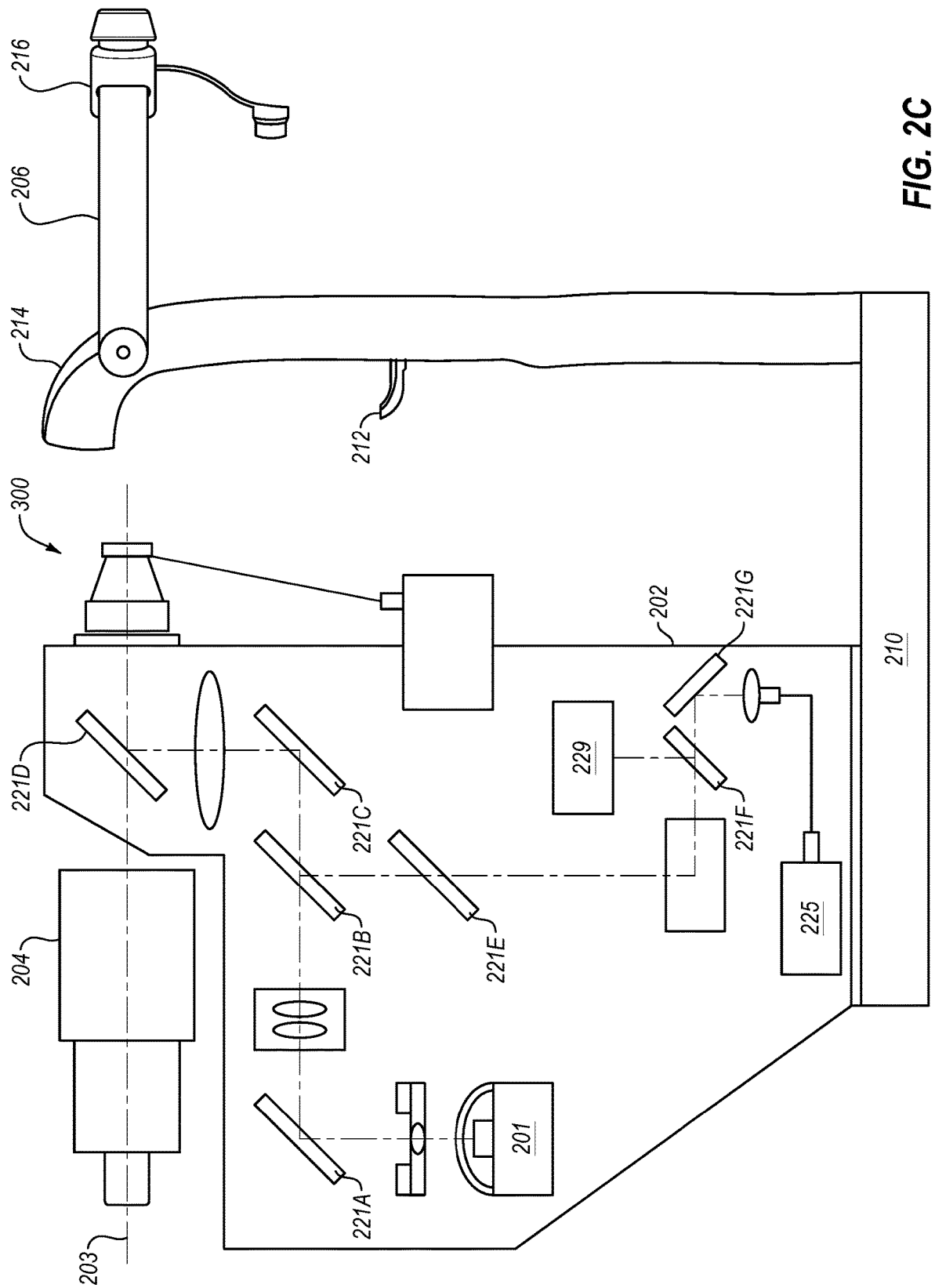
FIG. 2C illustrates another view of the system of FIG. 2A.

FIGS. 2A-2C illustrate an example laser-based ophthalmological treatment system 200 (hereinafter, "treatment system 200"), arranged in accordance with at least one embodiment described herein. FIG. 2A is an exterior side view of the treatment system 200. FIG. 2B is an exterior top view of the treatment system 200. FIG. 2C is a section view of the treatment system 200. The treatment system 200 may be configured to acquire a fundus image of a patient. The fundus image may be used to diagnosis an ocular disease (e.g., AMD, DME, CSC, and/or other conditions of the eye). For example, the treatment system may be configured to receive light reflected from the eye of the patient such as the eye 100 described with reference to FIG. 1A. The treatment system 200 may also be configured to administer laser-based treatment of the ocular disease. For example, in some embodiments, the treatment system 200 may be configured to emit therapeutic radiation into the eye of the patient. The therapeutic radiation may selectively damage retinal pigment epithelial (RPE) cells or other cells in a diseased portion of the eye. New cells may regenerate to replace the damaged cells, which may reduce or eliminate the effect of the ocular disease.

The treatment system 200 may include a device housing 202, a microscope 204, and a head fixation assembly 206. As shown in FIGS. 2A and 2B, the device housing 202, the microscope 204, and the head fixation assembly 206 may be visible. The device housing 202 may be positioned apart from the head fixation assembly 206 and may be fixed relative to the head fixation assembly 206. For instance, in some embodiments, the device housing 202 may be secured to a base 210 at a first location. The head fixation assembly 206 may also be secured to the base 210 at a second location. The head fixation assembly 206 may accordingly be fixed relative to the device housing 202. In some embodiments, the head fixation assembly 206 may be secured directly to the device housing 202 or otherwise fixed relative to the device housing 202.

The device housing 202 may surround or partially surround components of the treatment system 200. For instance, the device housing 202 may partially surround the microscope 204. A first portion of the microscope 204 into which a healthcare provider looks may be external to the device housing 202. A second portion of the microscope 204 (e.g., lenses, focus elements, etc.) may be positioned within the device housing 202. The microscope 204 may be positioned in a primary optical path 203 to allow an operator to view the eye of the patient.

The primary optical path 203 may be aligned with a center or a near center of a pupil of a patient during a treatment process and/or during a diagnosis process implemented using the treatment system 200. Generally, prior to acquiring a fundus image and administration of a therapeutic radiation, the pupil of a patient is aligned along the primary optical path 203. The therapeutic radiation may be emitted along the primary optical path 203. In addition, light captured in a fundus image travels along or substantially parallel to the primary optical path 203.

The head fixation assembly 206 may be configured to position and to retain a head of the patient relative to the device housing 202. Accordingly, once fixed within the head fixation assembly 206, the head of the patient may be positioned and retained relative to the device housing 202 and/or the microscope 204.

In some embodiments, the head fixation assembly 206 may include a jaw portion 212, a forehead rest 214, and a fixing band 216. A jaw of the patient may be placed in the jaw portion 212 and a forehead of the patient may be placed against the forehead rest 214. The fixing band 216 may be placed and tightened around the head to fix the head in the head fixation assembly 206.

FIG. 2C depicts an example arrangement of components that may be positioned within the device housing 202. In FIG. 2C, the treatment system 200 is depicted with a contact lens assembly 300. The contact lens assembly 300 may include one or more components that may be configured to redirect light reflected from a portion of an iris of the eye of the patient. The light reflected from the iris may be included on a fundus image that is generated by the treatment system 200. The iris included in the fundus image may be used to align or to assist in alignment of the fundus image. For example, during a diagnosis of an ocular disease, the iris may be used to align or orient a diseased portion of the fundus relative to the iris. Additionally, following acquisition of the fundus image, the light reflected from the portion of the iris may be used prior to administration of therapeutic radiation by the treatment system 200.

The treatment system 200 may include a photography device 225. The photography device 225 may be configured to acquire a fundus image of an eye that is aligned along the primary optical path 203. The fundus image may include a fundus fluorescein angiography (FFA), an indocyanine green chorioangiography (ICG), or another fundus image. The photography device 225 may include a photo sensor that may be configured to acquire the FFA, the ICG or the fundus image. The photography device 225 may be configured to receive light reflected from an eye of a patient in the head fixation assembly 206. The light may include a first portion that is reflected from a portion of the fundus. The light may also include a portion of the iris. Accordingly, the photography device 225 may include an image of the portion of the fundus along with the portion of the iris.

The light may be received via the contact lens assembly 300, which may be placed in contact with the eye of the patient in the head fixation assembly 206. The contact lens assembly 300 may be placed directly on a cornea of the eye. In previous systems, contact lens assemblies did not include an observing area that enabled reception by the contact lens assembly 300 of light reflected from the iris. Instead, the contact lens assemblies received light from the fundus.

In some embodiments, the contact lens assembly 300 may include a bifocal contact lens. The bifocal contact lens may include a portion that receives the light from the iris and redirects the light from the iris to the photography device 225. Some additional details of the bifocal contact lens are provided elsewhere in the present disclosure.

The photography device 225 may be positioned outside the primary optical path 203. The treatment system 200 may accordingly include one or more optical elements. The light may be redirected or transmitted by one or more optical elements 221D, 221B, 221E, 221F, and 221G to the primary optical path 203. In other embodiments, the photography device 225 may be positioned on the primary optical path 203.

The treatment system 200 may include a therapeutic radiation source 201. The therapeutic radiation source 201 may be configured to emit or transmit the therapeutic radiation. The therapeutic radiation may be emitted at least partially along the primary optical path 203.

The therapeutic radiation may be emitted through the contact lens assembly 300 and to the eye of the patient. The therapeutic radiation may be in a form of a pulsed laser. The therapeutic radiation may be configured to specifically target a layer of the retina of the eye such as the RPE cells (e.g., the RPE cells 122 of the retina 112 of FIGS. 1A-1C).

In an example embodiment, the therapeutic radiation is administered to the targeted RPE cells 122 in pulses with a pulse duration of between half a microsecond to several microseconds, such as 1.7 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. The administration of pulses may be terminated in response to feedback indicating a maximum exposure to the therapeutic radiation. In some embodiments, a pulse type and/or pulse control of the therapeutic radiation may be in a range of about 500 nanometers (nm) to about 600 nm or about 527 nm. Additionally or alternatively, the therapeutic radiation may be emitted in multiple pulses. For instance, the therapeutic radiation may be emitted in sets of between about 9 and about 20 pulses or about 15 pulses. In some other embodiments, the therapeutic radiation may include operating characteristics similar to those described in U.S. Pat. Nos. 7,115,120 and 7,836,894, which are incorporated herein by reference in their entireties.

In some embodiments, the therapeutic radiation may be generally more effective at treating conditions of the eye at higher exposure levels. However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

The therapeutic radiation source 201 may be positioned outside of the primary optical path 203. The therapeutic radiation may be redirected or transmitted by one or more of the optical elements 221A, 221B, 221C, and 221D to the primary optical path 203. In other embodiments, the therapeutic radiation source 201 may be positioned on the primary optical path 203.

Prior to emission of the therapeutic radiation by the therapeutic radiation source 201, a diseased portion of the eye may be diagnosed. Diagnosis of the diseased portion may be based on a fundus image of the eye. To acquire the fundus image, the head of the patient may be fixed in the head fixation assembly 206. For instance, the patient may place their jaw against the jaw portion 212 and may place their forehead against the forehead rest 214. The fixing band 216 may be placed around the head and tightened to fix the head relative to the head fixation assembly 206.

With the head of the patient fixed in the head fixation assembly 206, a portion of the fundus of the eye may be aligned with the primary optical path 203 of the treatment system 200. Following the alignment, the fundus image may be acquired by the photography device 225. The fundus image may include a portion of the fundus (e.g., the fundus 130 of FIG. 1A) that may include a diseased portion or an abnormality such as a fundus lesion. The fundus image may also include a portion of the iris. In particular, the fundus image may include the portion of the iris that surrounds the pupil. The iris may include one or more features that are unique or substantially unique. Based on the fundus image, the ocular disease may be diagnosed.

Additionally, the diseased portion or the abnormality may be positioned relative to the portion of the iris included in the fundus image. For example, the abnormality may be positioned to one or more features included in the iris and captured in the fundus image. In response to the diagnosis of the diseased portion, the patient may return one or more times for administration of the therapeutic radiation. To administer the therapeutic radiation by the treatment system 200, the head of the patient may be re-fixed in the head fixation assembly 206 such that the head may be fixed relative to the device housing 202 and components therein.

Using the fundus image that includes the portion of the iris, the portion of the fundus may be re-aligned with the primary optical path 203. For example, the diseased portion of the fundus may be identified based on its relationship to the portion of the iris in the fundus image. Additionally, the fundus image may be compared to the iris of the patient after the patient is re-fixed in the head fixation assembly 206. The patient may adjust their head until their eye aligns with the eye as depicted in the fundus image.

Following alignment, the therapeutic radiation may be emitted through a pupil of the eye to treat the diseased portion of the fundus. There may be multiple events in which the therapeutic radiation is administered.

In some embodiments, the therapeutic radiation source 201 may navigate to a position based on the fundus image. For instance, in some embodiments, the treatment system 200 may be configured to receive the light from the eye, compare a current portion of the iris with the portion of the iris in the fundus image. Based on the features in the iris and the position of the abnormality relative to the features of the iris in the fundus image, the therapeutic radiation source 201 may automatically navigate such that the therapeutic radiation is directed to the abnormality.

Figure 9:
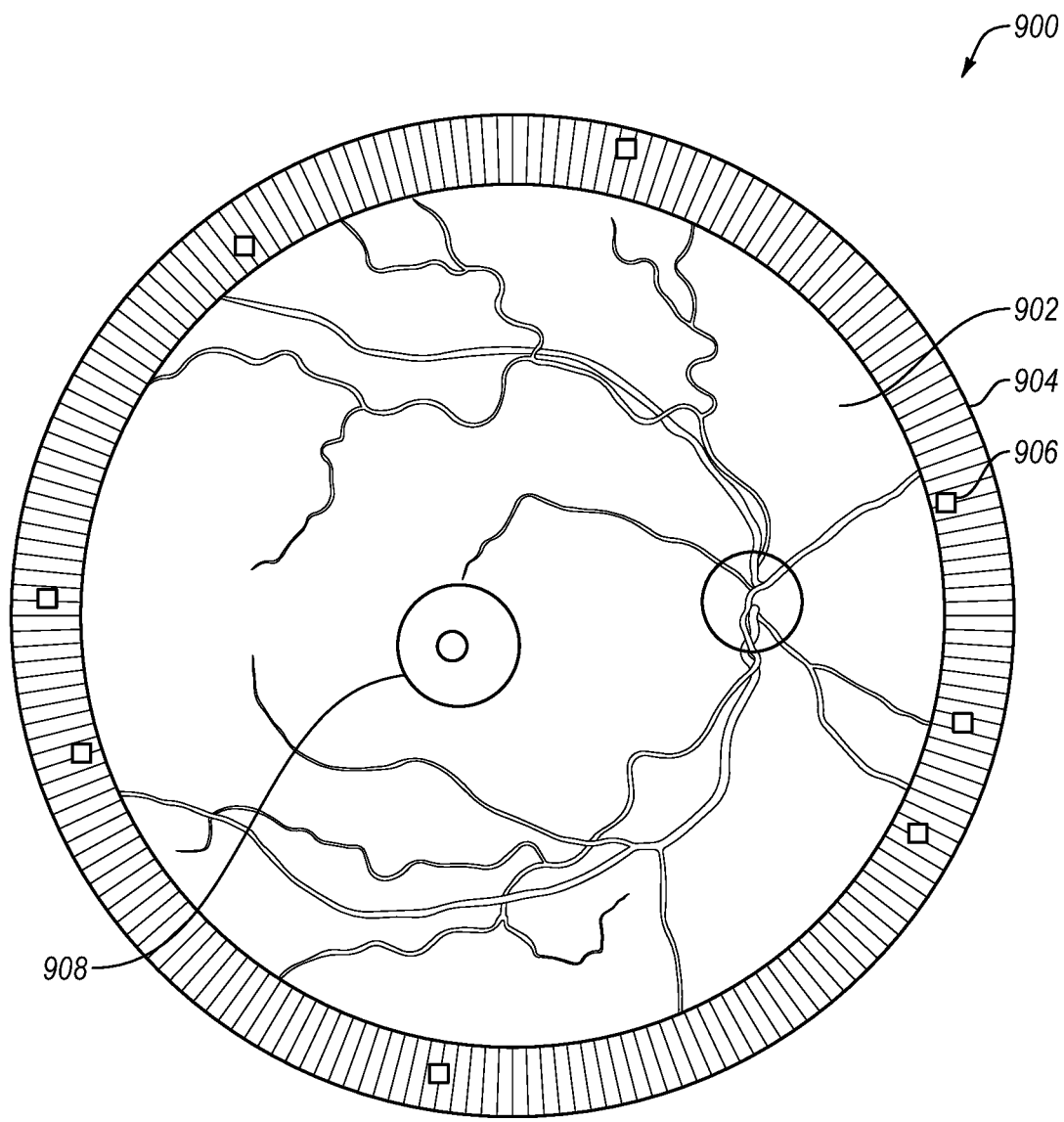
FIG. 9 is a block diagram of an example fundus image, all arranged in accordance with at least one embodiment of the present disclosure.

For example, with reference to FIG. 9, a block diagram of an example fundus image 900 is depicted. In the fundus image 900, a portion of a fundus 902 is included along with a portion of an iris 904. The portion of the iris 904 may include one or more features 906, only one of which is labeled in FIG. 9. An abnormality 908 may be located using the features 906 as reference. With combined reference to FIGS. 9 and 2C, when a patient returns for treatment, the therapeutic radiation source 201 may be navigated or aimed based on features of the iris of the patient.

During the treatment, in a clinic room, a healthcare profession may control ambient light, which may affect the iris 904. For instance, in some circumstance, a laser treatment may be carried out in a dark room. Additionally, the healthcare profession may administer a drug to perform mydriasis before the treatment. If a diameter size of a pupil (e.g., the pupil 106 of FIG. 1) changes, the iris 104 may expand or contract in a direction of the therapeutic radiation. Additionally still, the features 906 of the iris 904 may not rotate, and the position of the feature 906 on the iris 904 may be associated with a diameter of the pupil.

Referring back to FIG. 2C, the contact lens assembly 300 may be used to focus the light reflected from the eye. The contact lens assembly 300 may be disposable or may include one or more disposable portions. For instance, after use of the contact lens assembly 300 with a particular patient, the contact lens assembly 300 or one or more portions thereof may be discarded.

The contact lens assembly 300 may be positioned between the device housing 202 and the head fixation assembly 206. The contact lens assembly 300 may be placed directly on the eye of a patient. In some embodiments, the contact lens assembly 300 may be held in a hand of a healthcare provider during diagnosis and/or treatment of the eye of a patient. For instance, the healthcare provider may be positioned such that the healthcare provider may view and/or operate the microscope 204. With the head of the patient fixed in the head fixation assembly 206, the healthcare provider may hold the contact lens assembly 300 against the cornea of the eye of the patient. When the contact lens assembly 300 is placed on the cornea of the eye, the contact lens assembly 300 may be oriented along the primary optical path 203.

In some embodiments, the system may include a patient contact lens assembly retainer 205. The patient contact lens assembly retainer 205 may be coupled to the device housing 202. The patient contact lens assembly retainer 205 may be configured to selectively retain the contact lens assembly 300 relative to the device housing 202. For instance, instead of or in addition to the contact lens assembly 300 being held by the healthcare provider, the contact lens assembly 300 may be retained in the patient contact lens assembly retainer 205.

Figure 3:
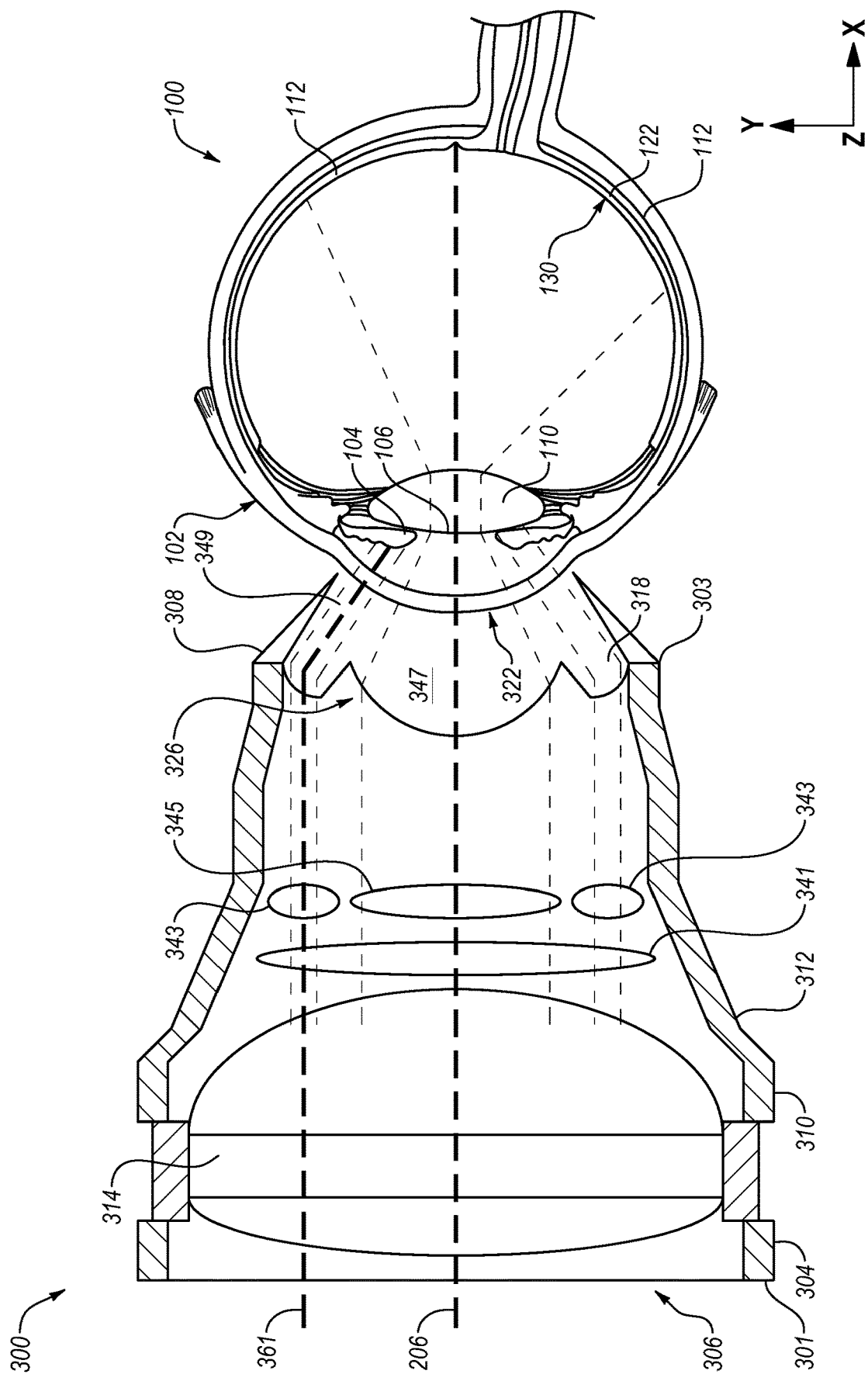
FIG. 3 is a block diagram of an example contact lens assembly that may be implemented in the system of FIGS. 2A-2C.

FIG. 3 illustrates an example embodiment of the contact lens assembly 300 that may be implemented in the treatment system 200 of FIGS. 2A-2C. In FIG. 3, the contact lens assembly 300 is depicted with the eye 100 of FIG. 1A. In FIG. 3, a sectional view of the contact lens assembly 300 is depicted.

The contact lens assembly 300 may include an assembly housing 304. The assembly housing 304 may define a first opening 306 at a first end 301 and a second opening 308 at a second end 303. The second opening 308 may be positioned opposite the first opening 306. The assembly housing 304 may include a generally cylindrical portion 310 that is connected to a generally conical portion 312. The first opening 306 may be defined by the generally cylindrical portion 310. The second opening 308 may be defined by the generally conical portion 312.

The input lens 314 may be positioned close to or at the first end 301. For example, the input lens 314 may be positioned in the generally cylindrical portion 310. Additionally or alternatively, the input lens 314 may be positioned at least partially in the first opening 306. The input lens 314 may be configured to transmit light 341 reflected from the fundus 130 of the eye 100 as well as a portion of the iris 104 to a treatment system such as the treatment system 200 of FIGS. 2A-2C. For example, with combined reference to FIGS. 2C and 3, the contact lens assembly 300 may be positioned along the primary optical path 203. In particular, the contact lens assembly 300 may be positioned such that the input lens 314 is oriented along the primary optical path 203. The contact lens assembly 300 may include a contact lens 318. The contact lens 318 may be positioned at least partially in the second opening 308 of the assembly housing 304. Between the contact lens 318 and the input lens 314, the contact lens assembly 300 may include an empty or substantially empty volume through which the light 341 may be transmitted.

The contact lens 318 may be positioned opposite the input lens 314. Accordingly, the light 341 may be reflected from the eye 100 and may enter the contact lens assembly 300 via the contact lens 318. The contact lens 318 may redirect the light 341. For instance, the contact lens 318 may redirect the light 341 such that the light 341 is substantially perpendicular to the primary optical path 203 or an angle between the light 341 and the primary optical path 203 is reduced.

The contact lens 318 may include bifocal characteristics. For example, the contact lens 318 may include two or more portions having two or more focal distances. Accordingly, portions of the light 341 received at different portions of the contact lens 318 may be affected differently. Additionally, portions of the contact lens 318 may be configured to receive and/or focus portions of the light 341 from a visual field that includes the pupil 106 as well as portions of the iris 104.

For instance, the contact lens 318 may include a central portion 347. A first portion 345 of the light 341 may pass through the central portion 347. The first portion 345 may be reflected from a portion of the fundus 130. For example, the first portion 345 may exit the eye 100 out the pupil 106 and enter the contact lens 318 through the contact surface 322. The first portion 345 of the light 341 may be focused or redirected as the first portion 345 passes through the central portion 347 of the contact lens 318. The redirection may include a reduction in an angle between the first portion 345 and the primary optical path 203 and/or may result in the first portion 345 being substantially parallel to the primary optical path 203.

The contact lens 318 may include an outer portion 349. The outer portion 349 may include a focal distance that is different from the focal distance of the central portion 347. Accordingly, the outer portion 349 may be configured to affect light differently and to focus light from a different distance than the central portion 347.

The outer portion 349 may surround or substantially surround the central portion 347. The outer portion 349 may be positioned on a secondary optical path 361. The secondary optical path 361 may include an annular shape that may converge through the outer portion 349 of the contact lens 318. The secondary optical path 361 may be radially displaced relative to the primary optical path 203. The secondary optical path 361 may impinge on or be aligned with the iris 104 or a portion thereof. For example, the secondary optical path 361 may be aligned with a portion of the iris 104 that surrounds the pupil 106.

A second portion 343 of the light 341 may be transmitted along the secondary optical path 361. The second portion 343 of the light 341 may be reflected from the iris 104 or from the portion of the iris 104 that surrounds the pupil 106. As the second portion 343 is transmitted through the outer portion 349 of the contact lens 318, the second portion 343 may be redirected. For instance, in some embodiments, the second portion 343 may be redirected such that the second portion 343 is substantially parallel to the primary optical path 203. In some embodiments, the second portion 343 may be redirected such that an angle between the primary optical path 203 and the second portion 343 is reduced.

The second portion 343 and the first portion 345 may be transmitted through the empty volume between the contact lens 318 and the input lens 314. The second portion 343 and the first portion 345 may be transmitted through the input lens 314 and to a treatment system such as the treatment system 200 of FIGS. 2A-2C. With combined reference to FIGS. 2C and 3, the light 341, that may include the first portion 345 and the second portion 343 may be communicated to the photography device 225. The photography device 225 may capture a fundus image of the fundus 130. The fundus image may include a portion of the iris 104. The light 341 may pass through the empty space between the contact lens 318 and the input lens 314, and may then pass through the input lens 314 before entering a treatment system.

The contact lens 318 may include a contact surface 322 and an interior surface 326. The contact surface 322 may be configured for direct physical contact with the eye 100. For example, the contact surface 322 may be curved to conform to the cornea 102 of the eye 100. The interior surface 326 may be positioned in the space between the input lens 314 and the contact lens 318.

The contact lens 318 of the contact lens assembly 300 may be configured to capture light from a portion of the iris 104. The contact lens 318 may be constructed in various ways. For example, FIGS. 4A-6B describe some embodiments of the contact lens 318. With the benefit of the present disclosure, one with skill in the art may appreciate that the contact lens 318 may differ from those depicted in FIGS. 4A-6B without departing from the scope of this disclosure.

Figure 4B:
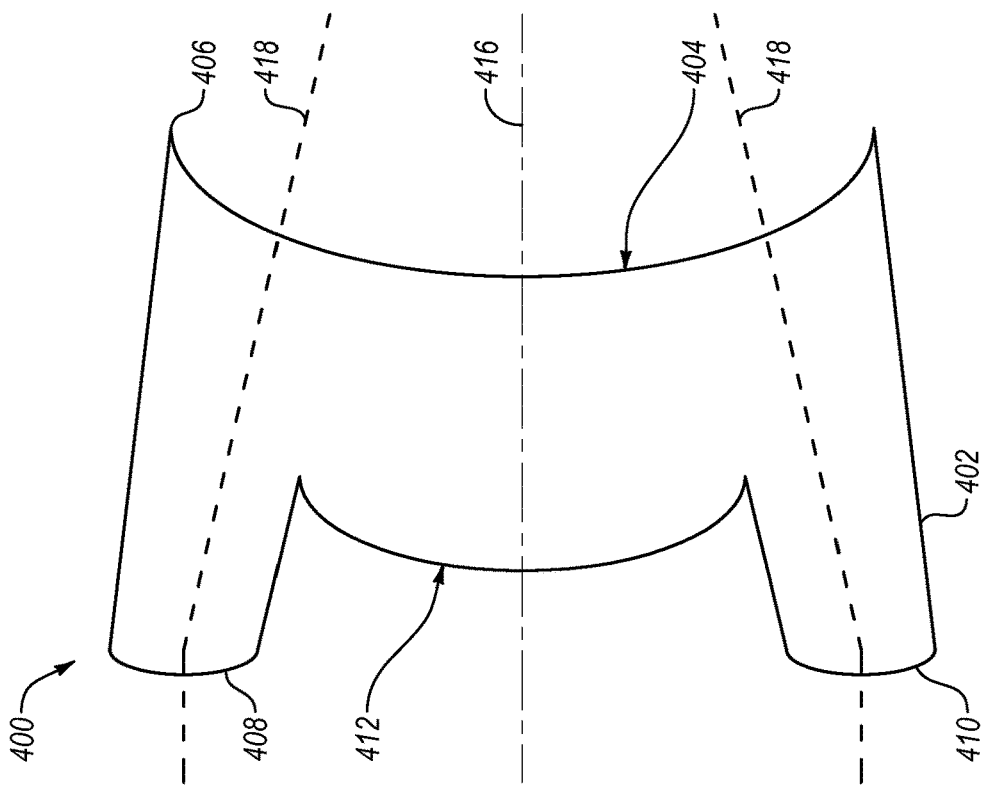
FIG. 4B is another view of the contact lens of FIG. 4A.
Figure 4A:
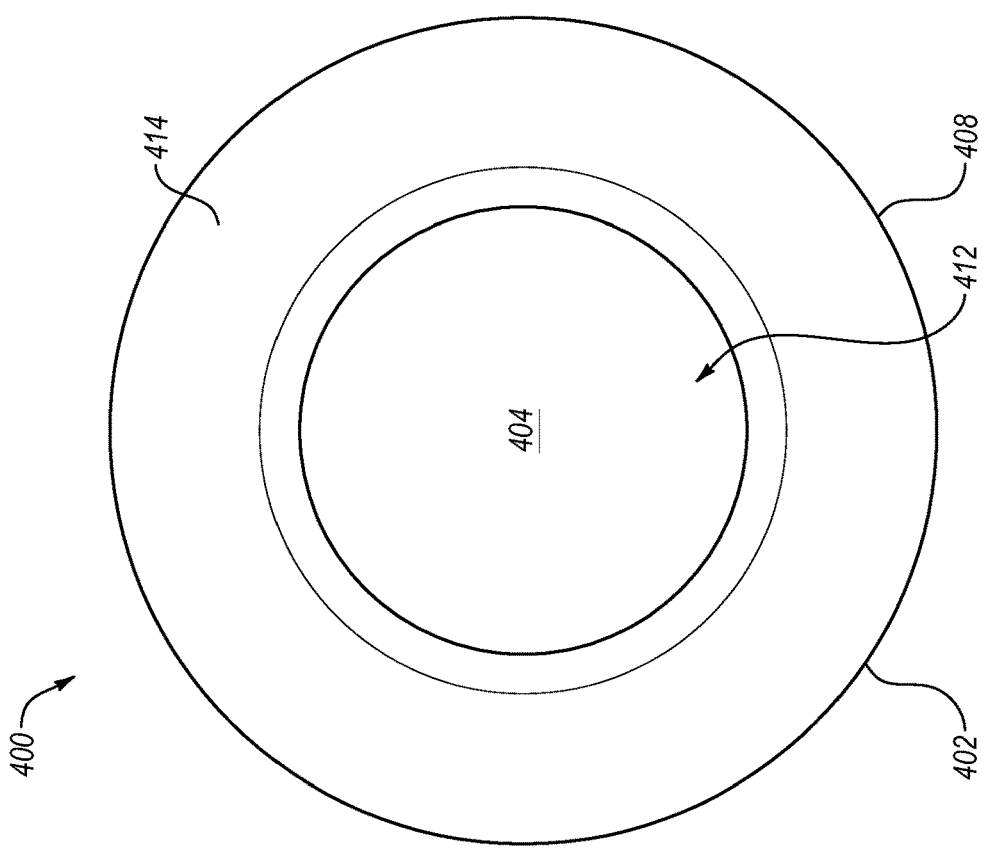
FIG. 4A is an example contact lens that may be implemented in the contact lens assembly of FIG. 3.

FIGS. 4A and 4B are block diagrams of an example contact lens 400 that may be implemented in the contact lens assembly 300 of FIG. 3. The contact lens 400 may have bifocal characteristics. FIG. 4A depicts an end view of the contact lens 400. FIG. 4B depicts a side, sectional view of the contact lens 400. The contact lens 400 may be substantially similar to and/or correspond to the contact lens 318 of FIG. 3.

The contact lens 400 may include a contact lens body 402. In some embodiments, the contact lens body 402 may be a unitary body. For instance, the contact lens body 402 may include a single piece of a polymer or a glass. In some embodiments, the contact lens body 402 may include multiple pieces (e.g., a central portion and an outer portion) that are mechanically coupled or adhered to one another.

The contact lens body 402 may include an exterior contact surface 404. The exterior contact surface 404 may be a concave surface. The concave surface may be configured to correspond, at least substantially, to a cornea of an eye. The exterior contact surface 404 may be located on a first end 406 of the contact lens body 402. The exterior contact surface 404 may be configured for direct physical contact with a cornea of an eye of a patient. For instance, during acquisition of a fundus image and/or during administration of a therapeutic radiation, the exterior contact surface 404 may be placed in direct physical contact with the cornea.

The contact lens 400 may include an annular bifocal surface 408. The annular bifocal surface 408 may be located on a second end 410 of the contact lens body 402. The second end 410 may be opposite or substantially opposite the exterior contact surface 404.

The annular bifocal surface 408 may include a central portion 412. The central portion may be a convex surface. The central portion 412 may include a first focal distance. The first focal distance may be configured to receive and/or focus light that is reflected from a portion of a fundus of a patient. For example, with combined reference to FIGS. 3 and 4B, the first focal distance may be configured to receive the first portion 345 of the light 341 that is reflected from the fundus 130 of the eye 100. Additionally, the first focal distance may be configured to focus therapeutic radiation onto a portion of the fundus such as a diseased portion or abnormality during treatment.

Referring back to FIGS. 4A and 4B, the central portion 412 may be positioned on a primary optical path 416. The primary optical path 416 may correspond to the primary optical path 203 of FIGS. 2C and 3. For instance, when a contact lens assembly that includes the contact lens 400 is being used in a diagnosis or treatment process, the primary optical path 416 may correspond to the primary optical path 203.

The annular bifocal surface 408 may include an outer portion 414. The outer portion 414 may extend from the central portion 412 substantially along the primary optical path 416. The outer portion 414 includes a concentric annular section defined in the annular bifocal surface 408 with the central portion 412.

The outer portion 414 may include a second convex surface. The outer portion 414 may surround at least a portion of the central portion 412. The outer portion 414 may include a second focal distance. The second focal distance may be configured to receive and/or focus light that is reflected from a portion of an iris of a patient. In particular, the second focal distance may be configured to receive and/or focus light reflected from a portion of an iris that surrounds a pupil of a patient. For example, with combined reference to FIGS. 3 and 4B, the second focal distance may be configured to receive the second portion 343 of the light 341 that is reflected from the iris 104 of the eye 100.

The outer portion 414 may be positioned on a secondary optical path 418. The secondary optical path 418 may be radially displaced relative to the primary optical path 416. The secondary optical path 418 may be configured to be optically aligned with a portion of an iris that surrounds the pupil during one or both of an imaging process and a treatment process. For example, during one or both of the imaging process and the treatment process, the secondary optical path 418 may correspond to the secondary optical path 361 of FIG. 3.

The contact lens 400 of FIGS. 4A and 4B may be configured to receive and focus light reflected from an eye of a patient. For instance, the contact lens 400 may receive a first portion of light reflected from a fundus of the eye in the central portion 412. The contact lens 400 may additionally receive a second portion of light reflected from an iris of the eye in the outer portion 414.

Figure 5B:
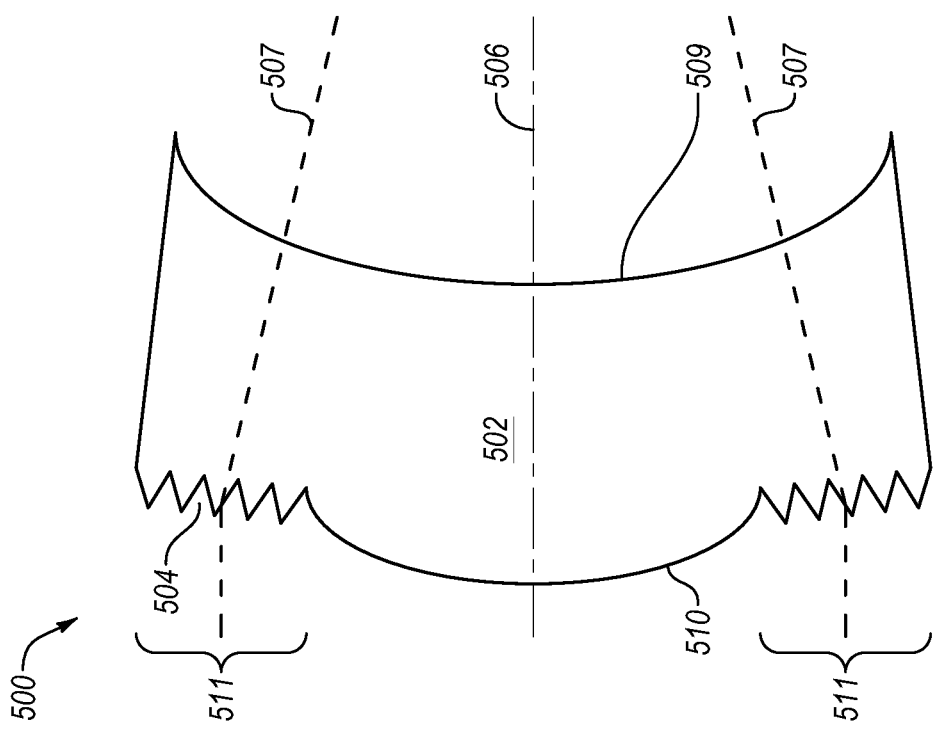
FIG. 5B is another view of the contact lens of FIG. 5A.
Figure 5A:
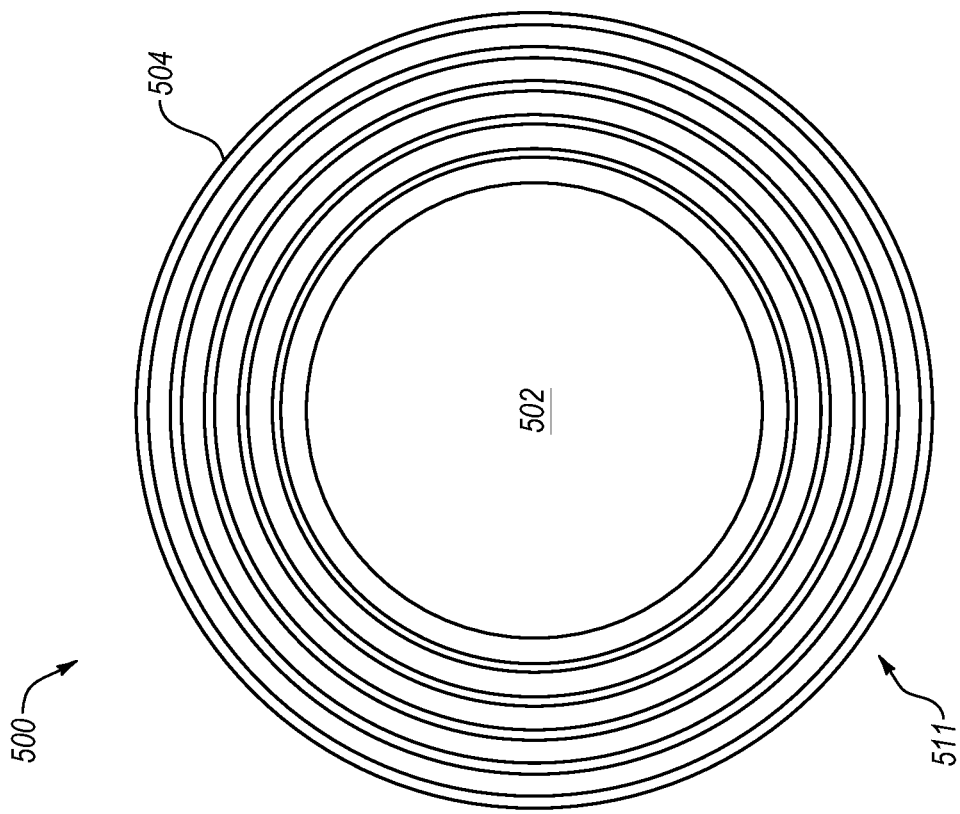
FIG. 5A depicts a block diagram of another example contact lens that may be implemented in the contact lens assembly of FIG. 3.

FIGS. 5A and 5B are block diagrams of another example contact lens 500 that may be implemented in the contact lens assembly 300 of FIG. 3. For example, the contact lens 500 is an example of the contact lens 318 of FIG. 3. FIG. 5A depicts an end view of the contact lens 500. FIG. 5B depicts a side, sectional view of the contact lens 500.

The contact lens 500 of FIGS. 5A and 5B may have bifocal characteristics. For instance, the contact lens 500 may include a central portion 502 and an outer portion 504. The central portion 502 may be positioned on or aligned along a primary optical path 506 (FIG. 5B) that may be aligned with a pupil of an eye of a patient when the head of the patient is retained in a head fixation assembly. For example, when the contact lens 500 is used with the contact lens assembly 300 of FIG. 3 and/or a treatment system such as the treatment system 200 of FIGS. 2A-2C, the central portion 502 may be positioned on or aligned along the primary optical path 203.

The central portion 502 may have a first focal distance. The first focal distance may enable focus of a first portion of light reflected from a fundus. In some embodiments, the central portion 502 may include one or more convex surfaces 509 and 510 or may include a convex lens, which may be configured to receive the first portion of light emitted from a pupil of a patient. For example, with combined reference to FIGS. 3 and 5B, the first focal distance may be configured to receive the first portion 345 of the light 341 that is reflected from the fundus 130 of the eye 100. Additionally, the first focal distance may be configured to focus therapeutic radiation and onto a portion of the fundus such as a diseased portion or abnormality during treatment.

The outer portion 504 may surround at least a portion of the central portion 502. The outer portion 504 may be positioned on a secondary optical path 507 that may be radially displaced relative to the primary optical path 506. The secondary optical path 507 may be annular. The secondary optical path 507 may be configured to be aligned with a portion of an iris that surrounds the pupil when the head is retained in the head fixation assembly. For example, when the contact lens 500 is used with the contact lens assembly 300 of FIG. 3 and/or a treatment system such as the treatment system 200 of FIGS. 2A-2C, the outer portion 504 may be positioned on or aligned along the secondary optical path 361.

The outer portion 504 may include a Fresnel lens 511. In some embodiments, the Fresnel lens 511 may include one or more stepped surfaces. The stepped surfaces may be concentric with the central portion 502. The multiple stepped surfaces may be cut or otherwise formed in the contact lens 500.

The Fresnel lens 511 may have a second focal distance or may effectively result in the second focal distance. The second focal distance may be configured to receive light reflected from a portion of an iris of the patient and redirect the light reflected from the portion of the iris. For example, the Fresnel lens 511 may be configured such that the light reflected from the portion of the iris is directed in a direction substantially parallel to the primary optical path 506. For example, with combined reference to FIGS. 3 and 5B, the second focal distance may be configured to receive the second portion 343 of the light 341 that is reflected from the iris 104 of the eye 100.

In some embodiments, the contact lens 500 may be a unitary body. For instance, the contact lens 500 may include a single piece of a polymer or a glass. In some embodiments, the contact lens 500 may include multiple pieces (e.g., a central portion and an outer portion) that are mechanically coupled or adhered to one another.

Figure 6B:
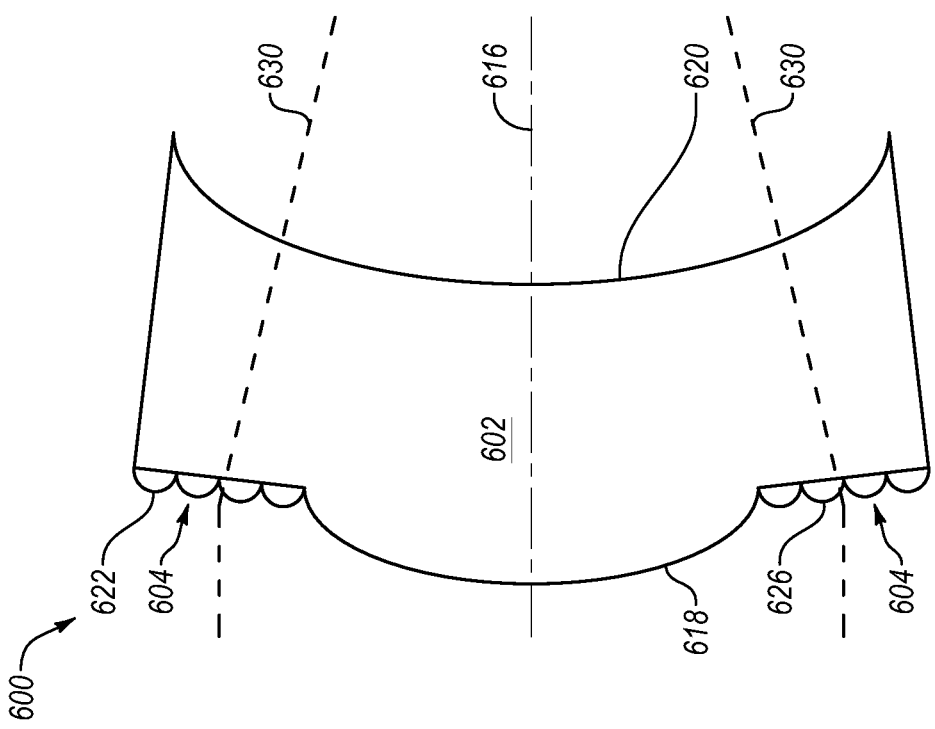
FIG. 6B is another view of the contact lens of FIG. 6A.
Figure 6A:
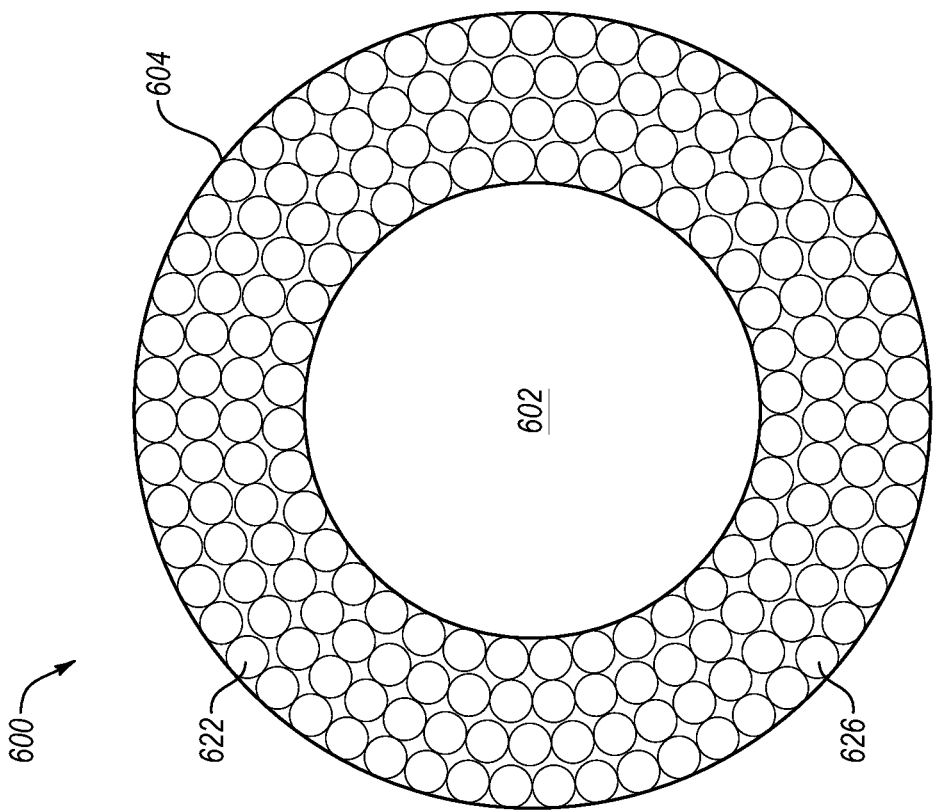
FIG. 6A depicts a block diagram of another example contact lens that may be implemented in the contact lens assembly of FIG. 3.

FIGS. 6A and 6B are block diagrams of another example contact lens 600 that may be implemented in the contact lens assembly 300 of FIG. 3. For example, the contact lens 600 is an example of the contact lens 318 of FIG. 3. FIG. 6A depicts an end view of the contact lens 600. FIG. 6B depicts a side, sectional view of the contact lens 600.

The contact lens 600 of FIGS. 6A and 6B may have bifocal characteristics. For instance, the contact lens 600 may include a central portion 602 and an outer portion 604. The central portion 602 may be positioned on or aligned along a primary optical path 616 (FIG. 6B) that may be aligned with a pupil of an eye of a patient when the head of the patient is retained in a head fixation assembly. For example, when the contact lens 600 is used with the contact lens assembly 300 of FIG. 3 and/or a treatment system such as the treatment system 200 of FIGS. 2A-2C, the central portion 602 may be positioned on or aligned along the primary optical path 616.

The central portion 602 may have a first focal distance. The first focal distance may enable the focus of a first portion of light reflected from a fundus. In some embodiments, the central portion 602 may include one or more convex surfaces 618 and 620 or may include a convex lens, which may be configured to receive the first portion of light emitted from a pupil of a patient. For example, with combined reference to FIGS. 3 and 6B, the first focal distance may be configured to receive the first portion 345 of the light 341 that is reflected from the fundus 130 of the eye 100. Additionally, the first focal distance may be configured to focus therapeutic radiation onto a portion of the fundus such as a diseased portion or abnormality during treatment. The outer portion 604 may surround at least a portion of the central portion 602. The outer portion 604 may be positioned on a secondary optical path 630 that may be radially displaced relative to the primary optical path 616. The secondary optical path 630 may be annular. The secondary optical path 630 may be configured to be aligned with a portion of an iris that surrounds the pupil when the head is retained in the head fixation assembly. For example, when the contact lens 600 is used with the contact lens assembly 300 of FIG. 3 and/or a treatment system such as the treatment system 200 of FIGS. 2A-2C, the outer portion 604 may be positioned on or aligned along the secondary optical path 630.

The outer portion 604 may include a microlens array 622. The microlens array 622 may include multiple microlenses 626, one of which is labeled in FIGS. 6A and 6B. One or more of the microlenses 626 may have a diameter that is less than about one millimeter (mm). For example, the microlenses 626 may have diameters between about 0.1 mm and 0.01 mm. The microlenses 626 may include multiple diameters within a range of about 0.01 mm to about 1 mm.

One or more of the microlenses 626 may include a spherical convex microlens, a micro-Fresnel lens, or another suitable structure. Additionally, the microlens array 622 may be formed in a one-dimensional or two-dimensional array. In some embodiments, one or more of the microlenses 626 may be constructed of a polymer-on-glass structure or another suitable structure.

The microlens array 622 may have a second focal distance. For example, in some embodiments, the microlenses 626 may result in the second focal distance. The second focal distance may be configured to receive light reflected from a portion of an iris of the patient and redirect the light reflected from the portion of the iris. For example, the microlens array 622 may be configured such that the light reflected from the portion of the iris is directed in a direction substantially parallel to the primary optical path 616.

For example, with combined reference to FIGS. 3 and 6B, the second focal distance may be configured to receive the second portion 343 of the light 341 that is reflected from the iris 104 of the eye 100.

Figure 7A:
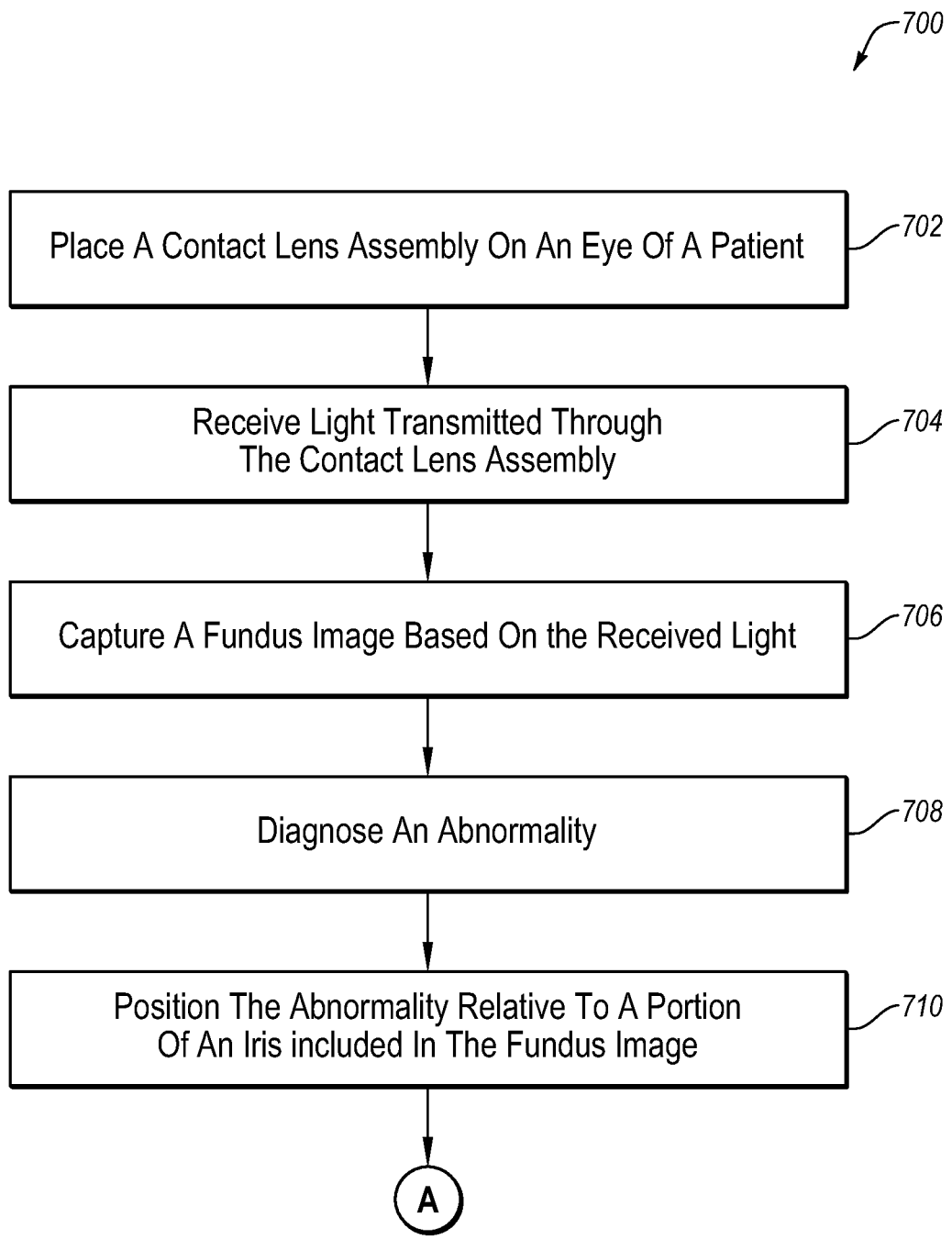
FIGS. 7A and 7B illustrate a flow diagram of an example method of image-based fundus alignment.
Figure 7B:
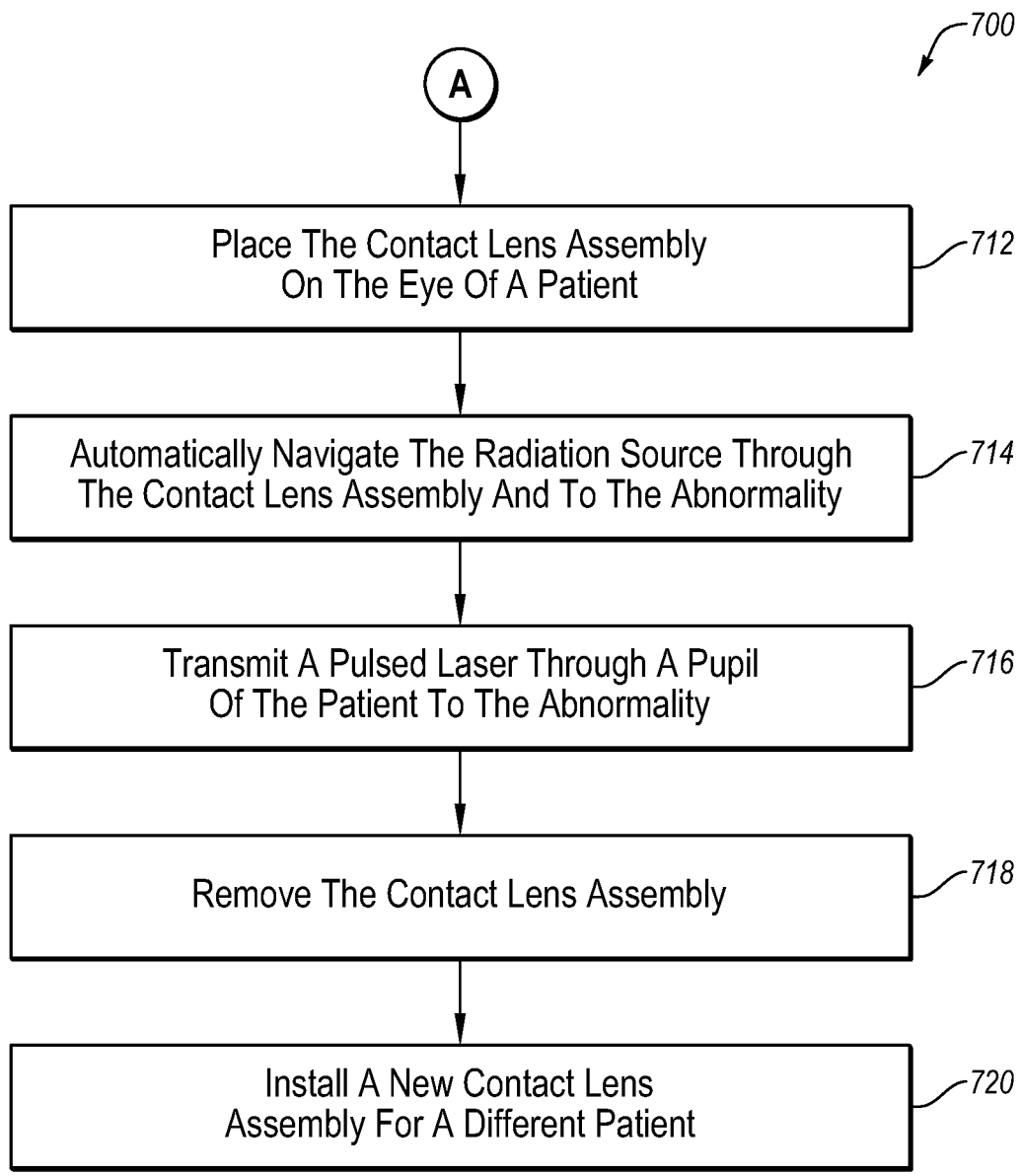

In some embodiments, the contact lens 600 may be a unitary body. For instance, the contact lens 600 may include a single piece of a polymer or a glass. In some embodiments, the contact lens 600 may include multiple pieces (e.g., a central portion and an outer portion) that are mechanically coupled or adhered to one another. FIGS. 7A and 7B illustrate a flow diagram of an example method 700 of image-based fundus alignment, arranged in accordance with at least some embodiments described herein. The method 700 may be implemented during a laser-based ophthalmological treatment.

The method 700 may be performed, in whole or in part, in the treatment system 200, the contact lens assembly 300, the contact lenses 318, 400, 500, 600, and/or in other systems and configurations. Alternatively or additionally, the method 700 may be implemented at least partially by a processor device that performs or controls performance of one or more of the operations of the method 700. For instance, a computer (such as the computing device 800 of FIG. 8) or another processor device may be communicatively coupled to the treatment system 200 and/or the contact lens assembly 300 may execute software or other computer-readable instructions accessible to the computer, e.g., stored on a non-transitory computer-readable medium accessible to the computer, to perform or control the treatment system 200 and/or the contact lens assembly 300 to perform the method 700 or a portion thereof.

The method 700 may include one or more of blocks 702, 704, 706, 708, 710, 712, 714, 716, 718, and 720. Although illustrated as discrete blocks, various blocks may be divided into additional blocks, supplemented with additional blocks, combined into fewer blocks, or eliminated, depending on the particular implementation. The method 700 may begin at block 702.

In block 702 ("Place A Contact Lens Assembly On An Eye Of A Patient"), a contact lens assembly may be placed on an eye of a patient. The contact lens assembly may be placed in an optical path that is optically aligned with a therapeutic radiation source and a photography device. For example, an exterior contact surface of the contact lens assembly may be positioned in direct physical contact with the eye of the patient. Block 702 may be followed by block 704.

In block 704 ("Receive Light Transmitted Through The Contact Lens Assembly"), light transmitted through the contact lens assembly may be received. For example, a photography device may receive the light transmitted through the contact lens assembly. The received light may include a first portion reflected from a portion of a fundus of the eye and transmitted through a central portion of a contact lens. The received light may also include a second portion reflected from a portion of an iris and transmitted through an outer portion of the contact lens. Block 704 may be followed by block 706.

In block 706 ("Capture A Fundus Image Based On The Received Light"), a fundus image may be captured based on the received light. For instance, in some embodiments, the fundus image may be captured by the photography device. The fundus image may include the portion of the fundus and the portion of the iris. Block 706 may be followed by block 708.

In block 708 ("Diagnose An Abnormality"), an abnormality may be diagnosed based at least partially on the fundus image. Block 708 may be followed by block 710. In block 710 ("Position The Abnormality Relative To A Portion Of An Iris Included In The Fundus Image"), the abnormality may be positioned relative to the portion of the iris included in the fundus image. Block 710 may be followed by block 712.

In block 712 ("Place The Contact Lens Assembly On The Eye Of A Patient"), the contact lens assembly may be placed on the eye of a patient. For instance, after the diagnosing, the contact lens assembly may be placed on the eye of a patient. Block 712 may be followed by block 714.

In block 714 ("Automatically Navigate The Radiation Source Through The Contact Lens Assembly And To The Abnormality"), the radiation source may be automatically navigated through the contact lens assembly and to the abnormality using the portion of the iris as a reference. Block 714 may be followed by block 716. In block 716 ("Transmit A Pulsed Laser Through A Pupil Of The Patient To The Abnormality"), a pulsed laser may be transmitted through a pupil of the patient to the abnormality. Block 716 may be followed by block 718.

In block 718 ("Remove The Contact Lens Assembly"), the contact lens assembly may be removed. For instance, in embodiments that include a laser-based ophthalmological treatment system, the contact lens may be removed from the laser-based ophthalmological treatment system after capturing the fundus image of a single patient. Block 718 may be followed by block 720.

In block 720 ("Install A New Contact Lens Assembly For A Different Patient"), a new contact lens assembly may be installed. For instance, the new contact lens assembly may be installed in the laser-based ophthalmological treatment system. The new contact lens assembly may be installed for a different patient.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Figure 8:
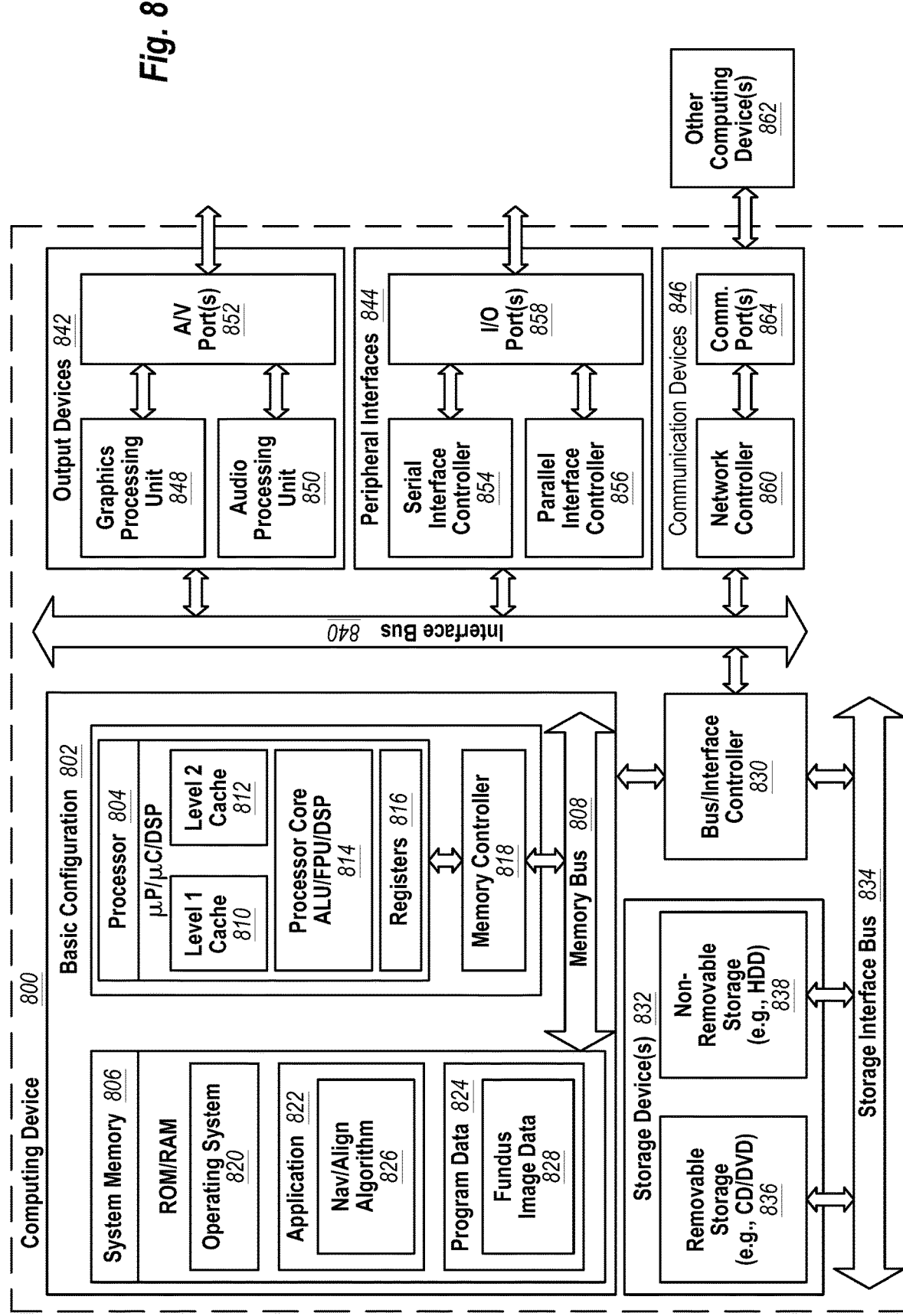
FIG. 8 is a block diagram of an example computing device.

FIG. 8 illustrates a block diagram of an example computing device 800, in accordance with at least one embodiment of the present disclosure. The computing device 800 may be used in some embodiments to perform or control performance of one or more of the methods and/or operations described herein. For instance, the computing device 800 may be communicatively coupled to and/or included in the treatment system 200 of FIGS. 2A-2C to perform or control performance of the method 700 of FIGS. 7A and 7B. In a basic configuration 802, the computing device 800 typically includes one or more processors 804 and a system memory 806. A memory bus 808 may be used for communicating between the processor 804 and the system memory 806.

Depending on the desired configuration, the processor 804 may be of any type including, such as a microprocessor (µP), a microcontroller (µC), a digital signal processor (DSP), or any combination thereof. The processor 804 may include one or more levels of caching, such as a level one cache 810 and a level two cache 812, a processor core 814, and registers 816. The processor core 814 may include an arithmetic logic unit (ALU), a floating point unit (FPU), a digital signal processing core (DSP Core), or any combination thereof. An example memory controller 818 may also be used with the processor 804, or in some implementations, the memory controller 818 may be an internal part of the processor 804.

Depending on the desired configuration, the system memory 806 may be of any type, such as volatile memory (such as RAM), non-volatile memory (such as ROM, flash memory, or the like), or any combination thereof. The system memory 806 may include an operating system 820, one or more applications 822, and program data 824. The application 822 may include a navigation/alignment algorithm 826 (in FIG. 8, "nav/align algorithm"). The navigation/alignment algorithm 826 may be configured to locate a disease portion of a fundus relative to features of an iris included in a fundus image and/or to navigate a radiation source relative to one or more elements of an iris. The program data 824 may include fundus image data 828. The fundus image data 828 may include fundus images that include features of an iris and/or locational information that locates a diseased portion of a fundus relative to the features. Additionally, the program data 824 may include information used to alter or adjust the system based on a comparison between the features of the iris and a position of a radiation source. In some embodiments, the application 822 may be arranged to operate with the program data 824 on the operating system 820 to perform one or more of the methods and/or operations described herein, including those described with respect to FIGS. 8A-8B. The computing device 800 may include additional features or functionality, and additional interfaces to facilitate communications between the basic configuration 802 and any other devices and interfaces. For example, a bus/interface controller 830 may be used to facilitate communications between the basic configuration 802 and one or more data storage devices 832 via a storage interface bus 834. The data storage devices 832 may include removable storage devices 836, non-removable storage devices 838, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer-readable instructions, data structures, program modules, or other data.

The system memory 806, the removable storage devices 836, and the non-removable storage devices 838 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 800. Any such computer storage media may be part of the computing device 800.

The computing device 800 may also include an interface bus 840 for facilitating communication from various interface devices (e.g., output devices 842, peripheral interfaces 844, and communication devices 846) to the basic configuration 802 via the bus/interface controller 830. The output devices 842 include a graphics processing unit 848 and an audio processing unit 850, which may be configured to communicate to various external devices such as a display or speakers via one or more A/V ports 852. The peripheral interfaces 844 include a serial interface controller 854 or a parallel interface controller 856, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 858. The communication devices 846 include a network controller 860, which may be arranged to facilitate communications with one or more other computing devices 862 over a network communication link via one or more communication ports 864.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 800 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 800 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A contact lens configured for use in a contact lens assembly for laser-based ophthalmological surgical treatments, the contact lens comprising:
   a contact lens body;
   an exterior contact surface on a first end of the contact lens body, wherein the exterior contact surface is concave and configured for direct physical contact with a cornea of an eye of a patient; and
   an annular bifocal surface on a second end of the contact lens body that is opposite the exterior contact surface, wherein the annular bifocal surface includes:
      a central portion that has a central convex surface that includes a first focal distance;
      an outer portion that surrounds at least a portion of the central portion and includes at least one outer surface that has a second focal distance; and
      a transition between the central convex surface and the at least one outer surface,
      wherein the central portion is positioned on a primary optical path that is configured to be aligned with a pupil of the eye during one or both of an imaging process and a treatment process; and
      wherein the outer portion is positioned on a secondary optical path that is radially displaced relative to the primary optical path, wherein the secondary optical path is configured to be optically aligned with a portion of an iris that surrounds the pupil during one or both of the imaging process and the treatment process.

2. The contact lens of claim 1, wherein the at least one outer surface of the outer portion includes at least one concentric annular section defined in the annular bifocal surface with the central portion.

3. The contact lens of claim 1, wherein the at least one outer surface of the outer portion includes a Fresnel lens.

4. The contact lens of claim 1, wherein the at least one outer surface of the outer portion includes a microlens array.

5. The contact lens of claim 1, wherein:
   the contact lens body is a unitary body; and
   the at least one outer surface of the outer portion includes a second convex surface.

6. A contact lens assembly configured for implementation in laser-based treatment, the contact lens assembly comprising:
   an assembly housing that defines a first opening and a second opening that is opposite the first opening;
   an input lens positioned in the first opening; and
   the contact lens of claim 1 positioned in the second opening.

7. The contact lens assembly of claim 6, wherein the at least one outer surface of the outer portion includes at least one of:
   at least one concentric annular section;
   a microlens array;
   a Fresnel lens; or
   a second convex surface.

8. A laser-based ophthalmological surgical system comprising:
   a therapeutic radiation source;
   a contact lens assembly optically coupled to the therapeutic radiation source;
   a head fixation assembly configured to position and retain a head of a patient with an eye of the patient optically aligned to the contact lens assembly to receive therethrough therapeutic radiation emitted by the therapeutic radiation source; and
   a microscope optically coupled to the contact lens assembly,
   wherein the contact lens assembly comprises a contact lens that includes an annular bifocal surface that comprises:
      a central portion that has a central convex surface with a first focal distance;
      an outer portion that surrounds at least a portion of the central portion and includes at least one outer surface that has a second local distance; and
      a transition between the central convex surface and the at least one outer surface,
      wherein the central portion is positioned on a primary optical path that is configured to be aligned with a pupil of the eye when the head is retained in the head fixation assembly, and
      wherein the outer portion is positioned on a secondary optical path that is radially displaced relative to the primary optical path, wherein the secondary optical path is configured to be optically aligned with a portion of an iris that surrounds the pupil when the head is retained in the head fixation assembly.

9. The laser-based ophthalmological surgical system of claim 8, wherein the contact lens assembly further comprises:
   an assembly housing; and
   an input lens positioned in a first opening that is defined in the assembly housing,
   wherein the contact lens is positioned in a second opening that is defined in the assembly housing.

10. The laser-based ophthalmological surgical system of claim 8, wherein the at least one outer surface of the outer portion includes at least one of:
    concentric annular section;
    a microlens array;
    a Fresnel lens; or
    a second convex surface.

11. The laser-based ophthalmological surgical system of claim 8, further comprising a patient contact lens assembly retainer configured to selectively retain the contact lens assembly in the laser-based ophthalmological surgical system, wherein the contact lens assembly is configured to be disposable and removable.

12. A method of image-based fundus alignment implemented during a laser-based ophthalmological treatment, the method comprising:
    providing a contact lens assembly with a contact lens,
    wherein the contact lens includes an annular bifocal surface comprising:
       a central portion that has a central convex surface that includes a first focal distance;
       an outer portion that surrounds at least a portion of the central portion and includes at least one outer surface that has a second focal distance; and
       a transition between the central convex surface and the at least one outer surface;

placing the contact lens assembly having the contact lens on an eye of a patient, wherein the contact lens assembly is placed in an optical path that is optically aligned with a therapeutic radiation source and a photography device;

receiving, by the photography device, light transmitted through the contact lens assembly, wherein the received light includes a first portion reflected from a portion of a fundus of the eye and transmitted through the central portion of the contact lens and the received light includes a second portion reflected from a portion of an iris of the eye and transmitted through the outer portion of the contact lens; and capturing, by the photography device, a fundus image based on the received light, wherein the fundus image includes the portion of the fundus and the portion of the iris.

13. The method of claim 12, further comprising:

diagnosing an abnormality based at least partially on the fundus image; and determining a position of the abnormality relative to the portion of the iris included in the fundus image.

14. The method of claim 13, further comprising:

after the diagnosing, placing the contact lens assembly on the eye of the patient; and automatically navigating the radiation source through the contact lens assembly and to the abnormality using the portion of the iris as a reference.

15. The method of claim 14, further comprising transmitting a short-pulse laser through a pupil of the patient to the abnormality.

16. The method of claim 12, further comprising:

positioning an exterior contact surface of the contact lens assembly in direct physical contact with the eye of the patient; and removing the contact lens assembly from a laser-based ophthalmological treatment system after capturing the fundus image of a single patient.

17. The method of claim 16, further comprising installing a new contact lens assembly in the laser-based ophthalmological treatment system for a different patient.

\* \* \* \* \*